US012234287B2

United States Patent
Uchida et al.

(10) Patent No.: US 12,234,287 B2
(45) Date of Patent: Feb. 25, 2025

(54) METHOD FOR ELICITING INFECTIOUS IMMUNOLOGICAL TOLERANCE

(71) Applicant: JUNTEN BIO Co., Ltd., Tokyo (JP)

(72) Inventors: Koichiro Uchida, Tokyo (JP); Kazuyoshi Takeda, Tokyo (JP); Ko Okumura, Tokyo (JP)

(73) Assignee: Junten Bio Co., Ltd., Tokyo (JP)

( * ) Notice: Subject to any disclaimer, the term of this patent is extended or adjusted under 35 U.S.C. 154(b) by 984 days.

(21) Appl. No.: 17/254,110

(22) PCT Filed: Jun. 21, 2019

(86) PCT No.: PCT/JP2019/024754
§ 371 (c)(1),
(2) Date: Dec. 18, 2020

(87) PCT Pub. No.: WO2019/245039
PCT Pub. Date: Dec. 26, 2019

(65) Prior Publication Data
US 2021/0261664 A1    Aug. 26, 2021

(30) Foreign Application Priority Data
Jun. 22, 2018  (JP) ................................ 2018-119003

(51) Int. Cl.
   *C07K 16/28*  (2006.01)
   *A61K 39/00*  (2006.01)
   *C12N 5/0783* (2010.01)
(52) U.S. Cl.
   CPC ...... *C07K 16/2818* (2013.01); *A61K 39/4611* (2023.05); *A61K 39/4621* (2023.05);
   (Continued)

(58) Field of Classification Search
   CPC ............ C07K 16/2818; C07K 16/2827; C07K 16/2896; C07K 2317/76; C07K 2319/30;
   (Continued)

(56) References Cited

FOREIGN PATENT DOCUMENTS

| JP | 2002-504120 A | 2/2002 |
|----|---------------|--------|
| JP | 2003-33175 A  | 2/2003 |

(Continued)

OTHER PUBLICATIONS

Pearl, Jeremy I., et al. Cell stem cell 8.3 (2011): 309-317 (Year: 2011).*

(Continued)

*Primary Examiner* — Jeremy C Flinders
*Assistant Examiner* — Thomas R. Amick
(74) *Attorney, Agent, or Firm* — Seed IP Law Group LLP

(57) ABSTRACT

The present disclosure provides a novel technique relating to immunological tolerance. More specifically, the present inventor found for the first time that, in a technique for inducing immunological tolerance by administering an organ transplantation patient (a recipient) a cell preparation containing cells in which anergy is induced by an inhibitor inhibiting the interaction between CD80/CD86 and CD28, the immunological tolerance continues even after the disappearance of the cells derived from the cell preparation from the recipient (infectious immunological tolerance). Further, the present inventor proved that such a cell preparation can elicit immunological tolerance against immunological rejection caused by allergy, iPS cells, etc. or cells, tissues or organs derived therefrom.

13 Claims, 13 Drawing Sheets

(52) U.S. Cl.
CPC .... *A61K 39/46434* (2023.05); *C07K 16/2827* (2013.01); *C07K 16/2896* (2013.01); *C12N 5/0637* (2013.01); *A61K 2239/38* (2023.05); *C07K 2317/76* (2013.01); *C07K 2319/30* (2013.01)

(58) Field of Classification Search
CPC .. C07K 16/28; A61K 2239/38; A61K 39/001; A61K 39/4611; A61K 2039/505; A61K 39/35; A61K 39/4621; A61K 39/46434; A61K 39/395; A61K 2300/00; C12N 2501/51; C12N 5/0637; A61P 37/06; A61P 37/08
See application file for complete search history.

(56) References Cited

FOREIGN PATENT DOCUMENTS

| | | | |
|---|---|---|---|
| JP | 2005-530762 A | 10/2005 | |
| JP | 2007-131598 A | 5/2007 | |
| JP | 2011-500730 A | 1/2011 | |
| JP | 2011-502163 A | 1/2011 | |
| JP | 2016-520081 A | 7/2016 | |
| KR | 10-2013-0049775 A | 5/2013 | |
| WO | 98/56417 A1 | 12/1998 | |
| WO | 03/094840 A2 | 11/2003 | |
| WO | 2009/052623 A1 | 4/2009 | |
| WO | 2009/058888 A1 | 5/2009 | |
| WO | 2011/113019 A2 | 9/2011 | |
| WO | 2014/186193 A1 | 11/2014 | |

OTHER PUBLICATIONS

Bashuda, "Immune tolerance in kidney transplantation Immune animals (monkeys), transplant," *Special Issue: Cutting Edge of Immune Tolerance Immune Tolerance in Kidney Transplantation—Medium Sized Animals (Monkeys)* 41(2):83-87, 2006 (w/English translation), 17 pages.

Bashuda et al., "Renal allograft rejection is prevented by adoptive transfer of anergic T cells in nonhuman primates," *J. Clin. Invest.* 115:1896-1902, 2005.

Davies et al., "Induction of Alloanergy in Human Donor T Cells Without Loss of Pathogen or Tumor Immunity," *Transplantation* 86:854-864, 2008.

Mori et al., "T cell anergy and immunotherapy," Molecular Biology of Allergy 2 170(12):993-997, 1994, (w/English translation), 17 pages.

Pacciani et al., "Induction of anergic allergen-specific suppressor T cells using tolerogenic dendritic cells derived from children with allergies to house dust mites," *J Allergy Clin Immunol* 125:727-736, 2010.

Steinbrink et al., "$CD4^+$ and $CD8^+$ anergic T cells induced by interleukin-10-treated human dendritic cells display antigen-specific suppressor activity," *Blood* 99:2468-2476, 2002.

Teraoka et al., "A Clinical Trial Aiming at Tolerance Induction by Adoptive Transfer of Ex Vivo-Induced, Donor-Specific Treg-Like Cells in Clinical Kidney Transplantation," *J Transplant Res* 2(1): doi http://dx.doi.org/10.16966/2473-1730.115, 2017, 8 pages.

Todo et al., "A Pilot Study of Operational Tolerance With a Regulatory T-Cell-Based Cell Therapy in Living Donor Liver Transplantation," *Hepatology* 64(2):632-643, 2016.

Cutolo et al., CTLA4-Ig interacts with cultured synovial macrophages from rheumatoid arthritis patients and downregulates cytokine production, *Arthritis Research & Therapy* 11:R176, 2009, 10 pages.

Davies, "Costimulatory blockade with monoclonal antibodies to induce alloanergy in donor lymphocytes," *Int J Hematol* 93:594-601, 2011.

Schumann et al., "Differences in CD44 Surface Expression Levels and Function Discriminates IL-17 and IFN-γ Producing Helper T Cells," *PLoS ONE* 10(7):e0132479, Jul. 14, 2015. (18 pages).

Topham et al., "Tissue-Resident Memory CD8+ T Cells: From Phenotype to Function," *Frontiers in Immunology* 9:515, Mar. 26, 2018. (10 pages).

Kalekar et al., "Relationship between CD4 Regulatory T Cells and Anergy In Vivo," *J Immunol* 198(7): 2527-2533, Apr. 1, 2017. (7 pages).

* cited by examiner

METHOD FOR ELICITING INFECTIOUS IMMUNOLOGICAL TOLERANCE

TECHNICAL FIELD

The present disclosure relates to a novel technology related to immune tolerance. More specifically, the present disclosure relates to a pharmaceutical composition comprising an anergic T cell, manufacture of the pharmaceutical composition, and quality control for the pharmaceutical composition.

BACKGROUND ART

Liver transplantation has been widely used as the final treatment on terminal liver failure patients. 20,000 or more liver transplantations are performed abroad, and more than 500 are performed in Japan annually.

Transplantation is one of the primary treatments chosen for terminal organ failure of the kidney, heart, liver, pancreas, or the like. Despite the dramatic advancement in the treatment of graft rejection in recent years, the majority of transplantations are ultimately rejected without any immunosuppressive regimen. Today's drug immunosuppressive regimen which is dependent on continuous drug therapy suppresses not only responses that are clearly directed to transplantation, but also all immune responses, such that organ transplant patients become more vulnerable to increased sensitivity to infections and cancer.

Such technologies for inducing immune tolerance include induction of an antigen specific non-immune response (anergy) of T cells. Specific technologies reported include a technology for directly administering an antibody which inhibits interactions between CD80/CD86 on antigen presenting cells and CD28 on unactivated (naïve) T cells to an organ transplant patient to induce donor antigen specific anergy in the body (Patent Literature 1) and a technology of co-culturing recipient cells and radiation irradiated donor cells in the presence of the same antibody to induce donor antigen specific anergic cells ex vivo and returning said cells to the recipient (Patent Literature 2, Patent Literature 3, and Non Patent Literatures 1 to 3).

CITATION LIST

Patent Literature

[PTL 1] Japanese National Phase PCT Laid-open Publication No. 2002-504120
[PTL 2] Japanese National Phase PCT Laid-open Publication No. 2007-131598
[PTL 3] Japanese National Phase PCT Laid-open Publication No. 2016-520081

Non Patent Literature

[NPL 1] Satoru Todo et al. Hepatorogy, 64 (vol. 2), 632-643 (2016)
[NPL 2] Teraoka S, Koyama I, Bashuda H, Uchida K, Tonsho M, et al. (2017) J Transplant Res 2 (1) p 1-8
[NPL 3] Bashuda H et al., J. Clin. Invest. 115:1896-1902 (2005).

SUMMARY OF INVENTION

Solution to Problem

The inventors found for the first time, as a result of diligent study, that immune tolerance persists (infectious immune tolerance), even if a cell formulation comprising cells having anergy induced with an inhibitory factor such as an antibody that inhibits an interaction between CD80/CD86 and CD28 is administered to an organ transplant patient (recipient) and a cell derived from the cell formulation is no longer present in the recipient (no longer detected) in a technology for inducing immune tolerance. The inventors further demonstrated that such a cell formulation can elicit immune tolerance to immune rejection caused by allergy or iPS cells or the like, or cell, tissue or organ derived therefrom.

Therefore, the present disclosure provides the following.

(1) A composition for eliciting permanent immune tolerance (infectious immune tolerance) to a donor in a subject, the composition comprising a cell having immune tolerance induced by mixing an inhibitory factor that can inhibit an interaction between CD80 and/or CD86 and CD28, a cell derived from the subject, and an antigen derived from the donor or a material containing the antigen.
(2) The composition of the preceding item, wherein the immune tolerance is immune tolerance elicited in a CD8 positive T cell in the subject.
(3) The composition of any of the preceding items, wherein the inhibitory factor is selected from the group consisting of a small molecule, a protein, a nucleic acid, a lipid, a saccharide, and a combination thereof.
(4) The composition of any of the preceding items, wherein the protein is an antibody or a variant thereof, or a cell surface molecule or a variant thereof.
(5) The composition of any of the preceding items, wherein the variant of the antibody is an antigen binding fragment.
(6) The composition of any of the preceding items, wherein the variant of the cell surface molecule is a fusion protein.
(7) The composition of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(8) The composition of any of the preceding items, wherein the CTLA4-Ig fusion protein is abatacept or belatacept.
(9) A method of preventing or treating a disease, disorder, or condition in a subject, the method comprising:
1) administering to the subject a formulation comprising a cell having anergy induced by mixing an inhibitory factor that can inhibit an interaction between CD80 and/or CD86 and CD28, a cell derived from the subject, and an antigen derived from the subject or an antigen that is not derived from the subject or a material containing the antigen; and
2) confirming an anergic state of a T cell of the subject, and if an anergic state can be confirmed, performing no additional treatment, and if an anergic state cannot be confirmed, re-administering a formulation comprising the cell.
(10) The method of any of the preceding items, wherein the formulation comprises a CD4 positive anergic cell, a CD8 positive anergic cell, or a combination thereof.
(11) The method of any of the preceding items, wherein the formulation comprises a CD8 positive anergic cell.

(12) The method of any of the preceding items, wherein the confirmation of an anergic state comprises confirming that the formulation comprising the cell is eliminated.
(13) The method of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.
(14) The method of any of the preceding items, wherein the disease, disorder, or condition comprises allergy.
(15) The method of any of the preceding items, wherein the disease, disorder, or condition comprises immune rejection caused by transplantation of an iPS cell or an ES cell or a cell, tissue, or organ derived therefrom.
(16) The method of any of the preceding items, wherein the inhibitory factor is selected from the group consisting of a small molecule, a protein, a nucleic acid, a lipid, a saccharide, and a combination thereof.
(17) The method of any of the preceding items, wherein the protein is an antibody or a variant thereof, or a cell surface molecule or a variant thereof.
(18) The method of any of the preceding items, wherein the variant of the antibody is an antigen binding fragment.
(19) The method of any of the preceding items, wherein the variant of the cell surface molecule is a fusion protein.
(20) The method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(21) The method of any of the preceding items, wherein the CTLA4-Ig fusion protein is abatacept or belatacept.
(22) A composition for treating or preventing allergy of a subject, the composition comprising a cell having immune tolerance induced by mixing an inhibitory factor that can inhibit an interaction between CD80 and/or CD86 and CD28, a cell derived from the subject, and an antigen which is a cause of allergy or a material containing the antigen.
(23) The composition of any of the preceding items, wherein the antigen which is a cause of allergy is selected from food, pollen, drug, and metal.
(24) A composition for suppressing or preventing immune rejection caused by an iPS cell or an ES cell or a cell, tissue, or organ derived therefrom in a subject, the composition comprising a cell having immune tolerance induced by mixing an inhibitory factor that can inhibit an interaction between CD80 and/or CD86 and CD28, a cell derived from the subject, and an antigen derived from the iPS cell or ES cell or a material containing the antigen.
(25) An anergy induced T cell, which is not a regulatory T cell.
(26) A method of manufacturing a T cell, which is not a regulatory T cell, having anergy to a subject induced, the method comprising:
A) mixing an inhibitory factor that can inhibit an interaction between CD80 and/or CD86 and CD28, a cell derived from the subject, and an antigen that is not derived from the subject or a material containing the antigen;
B) culturing the mixture to obtain a T cell; and
C) optionally stimulating the T cell with the antigen that is not derived from the subject or the material containing the antigen to confirm that the T cell does not react.
(27) The method of any of the preceding items, wherein the inhibitory factor is selected from the group consisting of a small molecule, a protein, a nucleic acid, a lipid, a saccharide, and a combination thereof.
(28) The method of any of the preceding items, wherein the protein is an antibody or a variant thereof, or a cell surface molecule or a variant thereof.
(29) The method of any of the preceding items, wherein the variant of the antibody is an antigen binding fragment.
(30) The method of any of the preceding items, wherein the variant of the cell surface molecule is a fusion protein.
(31) The method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(32) The method of any of the preceding items, wherein the CTLA4-Ig fusion protein is abatacept or belatacept.
(33) The T cell or method of any of the preceding items, wherein the T cell comprises a CD4 positive cell and/or a CD8 positive cell.
(34) A composition for inducing no reaction or a low reaction of a CD8 positive T cell within a subject to a specific antigen.
(35) A medicament for treating or preventing a disease, disorder, or condition caused by an antigen that is not derived from a subject, comprising a cell having immune tolerance induced by mixing an inhibitory factor that can inhibit an interaction between CD80 and/or CD86 and CD28, a cell derived from the subject, and an antigen derived from the subject or an antigen that is not derived from the subject or a material containing the antigen.
(36) The medicament of any of the preceding items, wherein the inhibitory factor is selected from the group consisting of a small molecule, a protein, a nucleic acid, a lipid, a saccharide, and a combination thereof.
(37) The medicament of any of the preceding items, wherein the protein is an antibody or a variant thereof, or a cell surface molecule or a variant thereof.
(38) The medicament of any of the preceding items, wherein the variant of the antibody is an antigen binding fragment.
(39) The medicament of any of the preceding items, wherein the variant of the cell surface molecule is a fusion protein.
(40) The medicament of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(41) The medicament of any of the preceding items, wherein the CTLA4-Ig fusion protein is abatacept or belatacept.
(42) The medicament of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.

(43) The medicament of any of the preceding items, wherein the disease, disorder, or condition comprises allergy.

(44) The medicament of any of the preceding items, wherein the disease, disorder, or condition comprises immune rejection caused by transplantation of an iPS cell or an ES cell or a cell, tissue, or organ derived therefrom.

(A1) A method of eliciting permanent immune tolerance (infectious immune tolerance) to a donor in a subject, the method comprising administering to the subject an effective amount of a cell having immune tolerance induced by mixing an inhibitory factor that can inhibit an interaction between CD80 and/or CD86 and CD28, a cell derived from the subject, and an antigen derived from the donor or a material containing the antigen.

(A2) The method of the preceding item, wherein the immune tolerance is immune tolerance elicited in a CD8 positive T cell in the subject.

(A3) The method of any of the preceding items, wherein the inhibitory factor is selected from the group consisting of a small molecule, a protein, a nucleic acid, a lipid, a saccharide, and a combination thereof.

(A4) The method of any of the preceding items, wherein the protein is an antibody or a variant thereof, or a cell surface molecule or a variant thereof.

(A5) The method of any of the preceding items, wherein the variant of the antibody is an antigen binding fragment.

(A6) The method of any of the preceding items, wherein the variant of the cell surface molecule is a fusion protein.

(A7) The method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(A8) The method of any of the preceding items, wherein the CTLA4-Ig fusion protein is abatacept or belatacept.

(A9) A method of treating or preventing allergy of a subject, the method comprising administering to the subject an effective amount of a cell having immune tolerance induced by mixing an inhibitory factor that can inhibit can interaction between CD80 and/or CD86 and CD28, a cell derived from the subject, and an antigen which is a cause of allergy or a material containing the antigen.

(A10) The method of any of the preceding items, wherein the antigen which is a cause of allergy is selected from food, pollen, drug, and metal.

(A11) A method of suppressing or preventing immune rejection caused by an iPS cell or an ES cell or a cell, tissue, or organ derived therefrom in a subject, the method comprising administering to the subject an effective amount of a cell having immune tolerance induced by mixing an inhibitory factor that can inhibit an interaction between CD80 and/or CD86 and CD28, a cell derived from the subject, and an antigen derived from the iPS cell or ES cell or a material containing the antigen.

(A12) A method of inducing no reaction or a low reaction of a CD8 positive T cell within a subject to a specific antigen.

(A13) A method of treating or preventing a disease, disorder, or condition caused by an antigen that is not derived from a subject, the method comprising administering to the subject an effective amount of a cell having immune tolerance induced by mixing an inhibitory factor that can inhibit an interaction between CD80 and/or CD86 and CD28, a cell derived from the subject, and an antigen derived from the subject or an antigen that is not derived from the subject or a material containing the antigen.

(A14) The method of any of the preceding items, wherein the inhibitory factor is selected from the group consisting of a small molecule, a protein, a nucleic acid, a lipid, a saccharide, and a combination thereof.

(A15) The method of any of the preceding items, wherein the protein is an antibody or a variant thereof, or a cell surface molecule or a variant thereof.

(A16) The method of any of the preceding items, wherein the variant of the antibody is an antigen binding fragment.

(A17) The method of any of the preceding items, wherein the variant of the cell surface molecule is a fusion protein.

(A18) The method of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(A19) The method of any of the preceding items, wherein the CTLA4-Ig fusion protein is abatacept or belatacept.

(A20) The method of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.

(A21) The method of any of the preceding items, wherein the disease, disorder, or condition comprises allergy.

(A22) The method of any of the preceding items, wherein the disease, disorder, or condition comprises immune rejection caused by transplantation of an iPS cell or an ES cell or a cell, tissue, or organ derived therefrom.

(B1) Use of a cell having immune tolerance induced by mixing an inhibitory factor that can inhibit an interaction between CD80 and/or CD86 and CD28, a cell derived from a subject, and an antigen derived from a donor or a material containing the antigen, for the manufacture of a medicament for eliciting permanent immune tolerance (infectious immune tolerance) to the donor in the subject.

(B2) The use of the preceding item, wherein the immune tolerance is immune tolerance elicited in a CD8 positive T cell in the subject.

(B3) The use of any of the preceding items, wherein the inhibitory factor is selected from the group consisting of a small molecule, a protein, a nucleic acid, a lipid, a saccharide, and a combination thereof.

(B4) The use of any of the preceding items, wherein the protein is an antibody or a variant thereof, or a cell surface molecule or a variant thereof.

(B5) The use of any of the preceding items, wherein the variant of the antibody is an antigen binding fragment.

(B6) The use of any of the preceding items, wherein the variant of the cell surface molecule is a fusion protein.
(B7) The use of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(B8) The use of any of the preceding items, wherein the CTLA4-Ig fusion protein is abatacept or belatacept.
(B9) Use of a cell having anergy induced by mixing an inhibitory factor that can inhibit an interaction between CD80 and/or CD86 and CD28, a cell derived from a subject, and an antigen derived from the subject or an antigen that is not derived from the subject or a material containing the antigen, for the manufacture of a medicament for preventing or treating a disease, disorder, or condition in the subject, wherein the cell is characterized by having an anergic state of a T cell of the subject confirmed, and if an anergic state can be confirmed, having no additional treatment performed, and if an anergic state cannot be confirmed, having a medicament comprising the cell re-administered.
(B10) The use of any of the preceding items, wherein the medicament comprises a CD4 positive anergic cell, a CD8 positive anergic cell, or a combination thereof.
(B11) The use of any of the preceding items, wherein the medicament comprises a CD8 positive anergic cell.
(B12) The use of any of the preceding items, wherein the confirmation of an anergic state comprises confirming that a formulation comprising the cell is eliminated.
(B13) The use of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.
(B14) The use of any of the preceding items, wherein the disease, disorder, or condition comprises allergy.
(B15) The use of any of the preceding items, wherein the disease, disorder, or condition comprises immune rejection caused by transplantation of an iPS cell or an ES cell or a cell, tissue, or organ derived therefrom.
(B16) The use of any of the preceding items, wherein the inhibitory factor is selected from the group consisting of a small molecule, a protein, a nucleic acid, a lipid, a saccharide, and a combination thereof.
(B17) The use of any of the preceding items, wherein the protein is an antibody or a variant thereof, or a cell surface molecule or a variant thereof.
(B18) The use of any of the preceding items, wherein the variant of the antibody is an antigen binding fragment.
(B19) The use of any of the preceding items, wherein the variant of the cell surface molecule is a fusion protein.
(B20) The use of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(B21) The use of any of the preceding items, wherein the CTLA4-Ig fusion protein is abatacept or belatacept.
(B22) Use of a cell having immune tolerance induced by mixing an inhibitory factor that can inhibit an interaction between CD80 and/or CD86 and CD28, a cell derived from a subject, and an antigen which is a cause of allergy or a material containing the antigen, for the manufacture of a medicament for treating or preventing allergy of the subject.
(B23) The use of any of the preceding items, wherein the antigen which is a cause of allergy is selected from food, pollen, drug, and metal.
(B24) Use of a cell having immune tolerance induced by mixing an inhibitory factor that can inhibit an interaction between CD80 and/or CD86 and CD28, a cell derived from a subject, and an antigen derived from an iPS cell or an ES cell or material containing the antigen, for the manufacture of a medicament for suppressing or preventing immune rejection caused by the iPS cell or an ES cell or a cell, tissue, or organ derived therefrom in the subject.
(B25) Use of a cell having immune tolerance induced by mixing an inhibitory factor that can inhibit an interaction between CD80 and/or CD86 and CD28, a cell derived from a subject, and an antigen derived from the subject or an antigen that is not derived from the subject or a material containing the antigen, for the manufacture of a medicament for treating or preventing a disease, disorder, or condition caused by an antigen that is not derived from the subject.
(B26) The use of any of the preceding items, wherein the inhibitory factor is selected from the group consisting of a small molecule, a protein, a nucleic acid, a lipid, a saccharide, and a combination thereof.
(B27) The use of any of the preceding items, wherein the protein is an antibody or a variant thereof, or a cell surface molecule or a variant thereof.
(B28) The medicament of any of the preceding items, wherein the variant of the antibody is an antigen binding fragment.
(B29) The use of any of the preceding items, wherein the variant of the cell surface molecule is a fusion protein.
(B30) The use of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.
(B31) The use of any of the preceding items, wherein the CTLA4-Ig fusion protein is abatacept or belatacept.
(B32) The use of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.
(B33) The use of any of the preceding items, wherein the disease, disorder, or condition comprises allergy.
(B34) The use of any of the preceding items, wherein the disease, disorder, or condition comprises immune rejection caused by transplantation of an iPS cell or an ES cell or a cell, tissue, or organ derived therefrom.
(C1) A cell having immune tolerance induced by mixing an inhibitory factor that can inhibit an interaction between CD80 and/or CD86 and CD28, a cell derived from a subject, and an antigen derived from a donor or a material containing the antigen, for eliciting permanent immune tolerance (infectious immune tolerance) to the donor in the subject.

(C2) The cell of the preceding item, wherein the immune (C2) tolerance is immune tolerance elicited in a CD8 positive T cell in the subject.

(C3) The cell of any of the preceding items, wherein the inhibitory factor is selected from the group consisting of a small molecule, a protein, a nucleic acid, a lipid, a saccharide, and a combination thereof.

(C4) The cell of any of the preceding items, wherein the protein is an antibody or a variant thereof, or a cell surface molecule or a variant thereof.

(C5) The cell of any of the preceding items, wherein the variant of the antibody is an antigen binding fragment.

(C6) The cell of any of the preceding items, wherein the variant of the cell surface molecule is a fusion protein.

(C7) The cell of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(C8) The cell of any of the preceding items, wherein the CTLA4-Ig fusion protein is abatacept or belatacept.

(C9) A cell having anergy induced by mixing an inhibitory factor that can inhibit an interaction between CD80 and/or CD86 and CD28, a cell derived from a subject, and an antigen derived from the subject or an antigen that is not derived from the subject or a material containing the antigen, for preventing or treating a disease, disorder, or condition in the subject, wherein the cell is characterized by having an anergic state of a T cell of the subject confirmed, and if an anergic state can be confirmed, having no additional treatment performed, and if an anergic state cannot be confirmed, having the cell re-administered.

(C10) The cell of any of the preceding items, wherein the cell is a CD4 positive anergic cell, a CD8 positive anergic cell, or a cell mixture comprising a combination thereof.

(C11) The cell of any of the preceding items, wherein the cell comprises a CD8 positive anergic cell.

(C12) The cell of any of the preceding items, wherein the confirmation of an anergic state comprises confirming that the cell is eliminated.

(C13) The cell of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.

(C14) The cell of any of the preceding items, wherein the disease, disorder, or condition comprises allergy.

(C15) The cell of any of the preceding items, wherein the disease, disorder, or condition comprises immune rejection caused by transplantation of an iPS cell or an ES cell or a cell, tissue, or organ derived therefrom.

(C16) The cell of any of the preceding items, wherein the inhibitory factor is selected from the group consisting of a small molecule, a protein, a nucleic acid, a lipid, a saccharide, and a combination thereof.

(C17) The cell of any of the preceding items, wherein the protein is an antibody or a variant thereof, or a cell surface molecule or a variant thereof.

(C18) The cell of any of the preceding items, wherein the variant of the antibody is an antigen binding fragment.

(C19) The cell of any of the preceding items, wherein the variant of the cell surface molecule is a fusion protein.

(C20) The cell of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(C21) The cell of any of the preceding items, wherein the CTLA4-Ig fusion protein is abatacept or belatacept.

(C22) Use of a cell having immune tolerance induced by mixing an inhibitory factor that can inhibit an interaction between CD80 and/or CD86 and CD28, a cell derived from a subject, and an antigen which is a cause of allergy or a material containing the antigen, for treating or preventing allergy of the subject.

(C23) The cell of any of the preceding items, wherein the antigen which is a cause of allergy is selected from food, pollen, drug, and metal.

(C24) Use of a cell having immune tolerance induced by mixing an inhibitory factor that can inhibit an interaction between CD80 and/or CD86 and CD28, a cell derived from a subject, and an antigen derived from an iPS cell or ES cell or a material containing the antigen, for suppressing or preventing immune rejection caused by the iPS cell or ES cell or a cell, tissue, or organ derived therefrom in the subject.

(C25) A cell having immune tolerance induced by mixing an inhibitory factor that can inhibit an interaction between CD80 and/or CD86 and CD28, a cell derived from a subject, and an antigen derived from the subject or an antigen that is not derived from the subject or a material containing the antigen, for treating or preventing a disease, disorder, or condition caused by an antigen that is not derived from the subject.

(C26) The cell of any of the preceding items, wherein the inhibitory factor is selected from the group consisting of a small molecule, a protein, a nucleic acid, a lipid, a saccharide, and a combination thereof.

(C27) The cell of any of the preceding items, wherein the protein is an antibody or a variant thereof, or a cell surface molecule or a variant thereof.

(C28) The cell of any of the preceding items, wherein the variant of the antibody is an antigen binding fragment.

(C29) The cell of any of the preceding items, wherein the variant of the cell surface molecule is a fusion protein.

(C30) The cell of any of the preceding items, wherein the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

(C31) The cell of any of the preceding items, wherein the CTLA4-Ig fusion protein is abatacept or belatacept.

(C32) The cell of any of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.

(C33) The cell of any of the preceding items, wherein the disease, disorder, or condition comprises allergy.

(C34) The cell of any of the preceding items, wherein the disease, disorder, or condition comprises immune rejection caused by transplantation of an iPS cell or an ES cell or a cell, tissue, or organ derived therefrom.

The present disclosure also provides the following.

(D1) A composition for eliciting permanent immune tolerance (infectious immune tolerance) to a donor in a subject, the composition comprising a cell having immune tolerance induced by mixing an antibody that can inhibit an interaction between CD80 and/or CD86 and CD28, a cell derived from the subject, and an antigen derived from the donor or a material containing the antigen.

(D2) The composition of the preceding item, wherein the immune tolerance is immune tolerance elicited in a CD8 positive T cell in the subject.

(D3) A method of preventing or treating a disease, disorder, or condition in a subject, the method comprising: 1) administering to the subject a formulation comprising a cell having anergy induced by mixing an antibody that can inhibit an interaction between CD80 and/or CD86 and CD28, a cell derived from the subject, and an antigen derived from the subject or an antigen that is not derived from the subject or a material containing the antigen; and 2) confirming an anergic state of a T cell of the subject, and if an anergic state can be confirmed, performing no additional treatment, and if an anergic state cannot be confirmed, re-administering a formulation comprising the cell.

(D3A) A medicament for preventing or treating a disease, disorder, or condition in a subject, wherein the medicament comprises a cell (e.g., T cell) having immune tolerance induced by mixing an antibody that can inhibit an interaction between CD80 and/or CD86 and CD28, a cell derived from the subject, and an antigen derived from the subject or an antigen that is not derived from the subject or a material the antigen, wherein the medicament is containing characterized by, after administering the medicament, having an anergic state of a T cell of the subject confirmed, and if an anergic state can be confirmed, having no additional treatment performed, and if an anergic state cannot be confirmed, having a medicament comprising the cell re-administered.

(D4) The method, medicament, or composition of any one of the preceding items, wherein the formulation comprises a CD4 positive anergic cell, a CD8 positive anergic cell, or a combination thereof.

(D5) The method, medicament, or composition of any one of the preceding items, wherein the formulation comprises a CD8 positive anergic cell.

(D6) The method, medicament, or composition of any one of the preceding items, wherein the confirmation of an anergic state comprises confirming that a formulation comprising the cell is eliminated.

(D7) The method, medicament, or composition of any one of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.

(D8) The method, medicament, or composition of any one of the preceding items, wherein the disease, disorder, or condition comprises allergy.

(D9) The method, medicament, or composition of any one of the preceding items, wherein the disease, disorder, or condition comprises immune rejection caused by transplantation of an iPS cell or an ES cell or a cell, tissue, or organ derived therefrom.

(D10) A composition for treating or preventing allergy of a subject, the composition comprising a cell having immune tolerance induced by mixing an antibody that can inhibit an interaction between CD80 and/or CD86 and CD28, a cell derived from the subject, and an antigen which is a cause of allergy or a material containing the antigen.

(D11) The composition of any one of the preceding items, wherein the antigen which is a cause of allergy is selected from food, pollen, drug, and metal.

(D11A) The composition of item D10 to D11, further comprising a feature of any one or more of items D1 to D9.

(D12) A composition for suppressing or preventing immune rejection caused by an iPS cell or an ES cell or a cell, tissue, or organ derived therefrom in a subject, the composition comprising a cell having immune tolerance induced by mixing an antibody that can inhibit an interaction between CD80 and/or CD86 and CD28, a cell derived from the subject, and an antigen derived from the iPS cell or ES cell or a material containing the antigen.

(D12A) The composition of item D12, further comprising a feature of any one or more of items D1 to D11.

(D13) An anergy induced T cell, which is not a regulatory T cell.

(D13A) The composition of item D13, further comprising a feature of any one or more of items D1 to D11, D11A, D12, and D12A.

(D14) A method of manufacturing a T cell, which is not a regulatory T cell, having anergy to a subject induced, the method comprising: A) mixing an antibody that can inhibit an interaction between CD80 and/or CD86 and CD28, a cell derived from the subject, and an antigen that is not derived from the subject or a material containing the antigen; B) culturing the mixture to obtain a T cell; and C) optionally stimulating the T cell with the antigen that is not derived from the subject or the material containing the antigen to confirm that the T cell does not react.

(D15) The T cell of any one of the preceding items or the method of any one of the preceding items, wherein the T cell comprises a CD4 positive cell and/or a CD8 positive cell.

(D15A) The method of any one of the preceding items, further comprising a feature of any one or more of items D1 to D11, D11A, D12, D12A, and D13.

(D16) A composition for inducing no reaction or a low reaction of a CD8 positive T cell within a subject to a specific antigen.

(D16A) The composition of any one of the preceding items, further comprising a feature of any one or more of items D1 to D11, D11A, D12, D12A, D13, D14, D15, and D15A.

(D17) A medicament for treating or preventing a disease, disorder, or condition caused by an antigen that is not derived from a subject, comprising a cell having immune tolerance induced by mixing an antibody that can inhibit an interaction between CD80 and/or CD86 and CD28, a cell derived from the subject, and an antigen derived from the subject or an antigen that is not derived from the subject or a material containing the antigen.

(D18) The medicament of any one of the preceding items, wherein the disease, disorder, or condition is selected from the group consisting of graft rejection, allergy, autoimmune disease, graft-versus-host disease, and immune rejection caused by transplantation of an iPS cell or an ES cell or a cell, tissue, or organ derived therefrom.

(D19) The medicament of any one of the preceding items, wherein the disease, disorder, or condition comprises allergy.

(D20) The medicament of any of the preceding items, wherein the disease, disorder, or condition comprises immune rejection caused by transplantation of an iPS cell or an ES cell or a cell, tissue, or organ derived therefrom.

(D20A) The medicament of any one of the preceding items, further comprising a feature of any one or more of items D1 to D11, D11A, D12, D12A, D13, D14, D15, D15A, D16, D16A, and D17 to D19.

The present disclosure is intended so that one or more of the features described above can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

The composition of the present disclosure can elicit permanent immune tolerance (infectious immune tolerance) to a donor. Quality of a medicament can also be controlled in the manufacture of a medicament for inducing immune tolerance, with a CD8 positive cell as an indicator. The composition of the present disclosure can treat allergy and suppress immune rejection of an iPS cell or an ES cell or a cell, tissue, or organ derived therefrom.

BRIEF DESCRIPTION OF DRAWINGS

FIG. 2a conducted an experiment by the methodology shown in the left panel. The results thereof (engraftment rate of heart) are shown in the bottom right graph. The engraftment rate of transplanted heart is improved by infusion of anergic cells in a cell count dependent fashion. Improvement in the survival (improvement in the engraftment rate) of a transplanted heart of 100 days or longer was observed in all mice from infusion of $6 \times 10^6$ anergic cells, which demonstrates induction of immune tolerance to the transplanted heart. FIG. 2b is the result of investigating whether infused anergic cells are detected in the peripheral blood (PBMC), lymph node (MLN), spleen, and transplanted heart (Transplant Heart). Immune tolerant BALB/c heart transplantation indicates a B6 mouse transplanted with a heart of an allo BALB/c mouse infused with anergic cells, and immune tolerant B6 heart transplantation indicates a B6 mouse transplanted with a heart of a syngenic B6 mouse infused with anergic cells. Infused anergic cells were undetected by fluorescent expression not only in the peripheral blood, lymph node, and spleen, but also in the transplanted heart.

FIG. 3a shows, from the left, a molecular weight marker, 1: NC no template, 2: PC GFP mouse genomic DNA, 3: 1/100 diluted GFP mouse genomic DNA, 4: 1/1000 diluted GFP mouse genomic DNA, 5: 1/10000 diluted GFP mouse genomic DNA, 6: 1/100000 diluted GFP mouse genomic DNA, and 7: wild-type mouse genomic DNA. As shown, Example 2 was conducted using a GFP gene in the genomic gene that can be detected even at 0.1% (presence of 1/1000 diluted GFP mouse genomic DNA: lane 4) under PCR conditions. The results are shown in FIG. 3b. FIG. 3b shows, on the top row from the left, PBMC and spleen and, on the bottom row from the left, lymphocyte (MLN) and heart. Each lane indicates, from the left, molecular weight marker (M), 1: no NC template, 2: PC (positive control: GFP mouse lymphocyte genomic DNA), 3:3 days after transplantation, 4:1 week after transplantation, 5:4 weeks after transplantation, 6:7 weeks after transplantation, and 7:15 weeks after transplantation (immune tolerance).

FIG. 4 shows the engraftment rate of heart after infusion of anergic cells derived from a B6 mouse stimulated with Balb/C mouse splenocytes in the presence of anti-CD80/86 antibodies into a B6 mouse. It is shown that rejection of the transplanted BALB/c mouse heart was inhibited 100% and the heart was surviving after 100 days, whereas a heterologous ($3^{rd}$ party) CBA mouse heart quickly induced rejection after transplantation, and the heart was rejected 100% at about 50 days.

FIG. 8 shows evaluation of immunosuppression ability performed in Example 5.

FIG. 8 shows evaluation of immunosuppression ability performed in Example 5. FIG. 8c shows the production of IL-2 (left) and IL-10 (right). Each graph shows, from the left, naïve responder cells only, stimulation by allo cells of CD4 positive naïve cells, stimulation by allo cells of CD4 positive naïve cells upon addition of 1st anergic cells, stimulation by allo cells of CD4 positive naïve cells upon addition of 2nd anergic cells, and stimulation by allo cells of CD4 positive naïve cells upon addition of 3rd anergic cells. It was demonstrated that each of the 1st anergic cells, 2nd anergic cells, and 3rd anergic cells suppressed the production of cytokine IL-2 that induces cell proliferation from responder CD4 positive cells, while inducing the production of representative cytokine IL-10 that suppresses immune responses. Each graph shows the ratio when the amount of production of each cytokine under the condition of only responder cells (no stimulation) is assumed to be 1.

FIG. 8 shows evaluation of immunosuppression ability performed in Example 5. FIG. 8c shows the production of IL-2 (left) and IL-10 (right). Each graph shows, from the left, naïve responder cells only, stimulation by allo cells of CD4 positive naïve cells, stimulation by allo cells of CD4 positive naïve cells upon addition of 1st anergic cells, stimulation by allo cells of CD4 positive naïve cells upon addition of 2nd anergic cells, and stimulation by allo cells of CD4 positive naïve cells upon addition of 3rd anergic cells. It was demonstrated that each of the 1st anergic cells, 2nd anergic cells, and 3rd anergic cells suppressed the production of cytokine IL-2 that induces cell proliferation from responder CD4 positive cells, while inducing the production of representative cytokine IL-10 that suppresses immune responses. Each graph shows the ratio when the amount of production of each cytokine under the condition of only responder cells (no stimulation) is assumed to be 1.

FIG. 10 shows results indicating the reaction of CD8 positive T cells to a donor.

FIG. 10 shows results indicating the reaction of CD8 positive T cells to a donor.

FIG. 10 shows results indicating the reaction of CD8 positive T cells to a donor.

FIG. 12a shows the number of leucocytes contained in bronchial effusion (BAL). FIG. 12b shows the number of eosinophils contained in BAL. FIG. 12c shows the amount of IL-4 contained in BAL. Each graph shows, from the left, mouse given only phosphate buffered saline control), ovalbumin stimulated mouse (OVA challenge), and mouse given ovalbumin stimulation and the anergic cells of the present disclosure (cellular therapy).

FIG. 15 shows results of eliciting immune tolerance in the food allergy model shown in FIG. 13.

FIG. 15 shows results of eliciting immune tolerance in the food allergy model shown in FIG. 13.

FIG. 15 shows results of eliciting immune tolerance in the food allergy model shown in FIG. 13.

DESCRIPTION OF EMBODIMENTS

Figure 1:
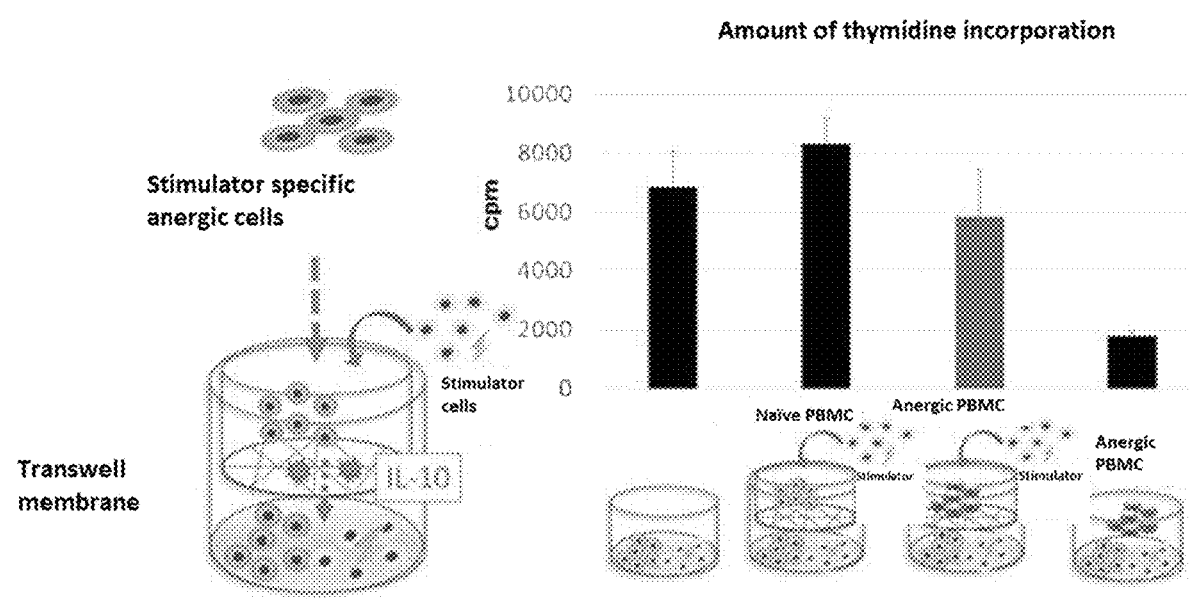
FIG. 1 shows the scheme of experiment conducted in Example 1 (left panel and the bottom part of the right panel) and the results thereof (top part of the right panel). The results in the top part of the right panel shows the thymidine incorporation. The left side shows a proliferative reaction of responder cells due to stimulator cell stimulation. Second from the left shows the amount when fresh responder cells and stimulator cells are placed in the top row. The second from the right shows the amount when anergic cells and stimulator cells are placed in the top row. The right end shows the amount when anergic cells are placed in the same row as stimulator cells/responder cells.

The present disclosure is described hereinafter while providing the best mode of the present disclosure. Throughout the entire specification, a singular expression should be understood as encompassing the concept thereof in the plural form, unless specifically noted otherwise. Thus, singular articles (e.g., "a", "an", "the" and the like in case of English) should also be understood as encompassing the concept thereof in the plural form, unless specifically noted otherwise. The terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

Definitions of Terms

As used herein, "about" refers to a range of ±10% of the subsequent numerical value.

As used herein, "immune tolerance" refers to a state where a specific immune response to a specific antigen is not exhibited or a specific immune response is suppressed. Immune tolerance can also refer to either or both of a state where an immune cell (especially T cell) does not exhibit a specific immune response to a specific antigen or a specific immune response is suppressed, and a state where a human does not exhibit a specific immune response to a specific antigen or a specific immune response is suppressed. Immune tolerance has drawn attention because elicitation of immune tolerance makes it possible to treat immune rejection or treat allergies. As used herein, "anergy" refers to a state where costimulation is not inputted when an antigen is presented from an antigen presenting cell so that a cell cannot respond upon stimulated under the condition with costimulation the next time. Therefore, as used herein, "anergic cell" refers to a (non-immune responsive) cell with immune tolerance, and "anergic T cell" is a (non-immune responsive) T cell with immune tolerance, which also encompasses T cells that are not activated as well as T cells that are non-responsive when encountering the same antigen again. As used herein, "PBMC (or T cell) with immune tolerance induced" is synonymous with "anergic PBMC (or T cell)". It is possible to verify whether a cell is such a cell by, for example, verifying that the cell is CD44 positive, but the method is not limited thereto.

As used herein, "subject" includes domesticated animals (e.g., cows, sheep, cats, dogs, and horses), primates (e.g., humans and non-human primates such as monkeys), rabbits, and rodents (e.g., mice and rats). In a specific embodiment, the subject is a human.

As used herein, "permanent immune tolerance (infectious immune tolerance)" refers to maintenance of immune tolerance to a specific antigen at least for a certain period of time (e.g., several months, 1 year, or 3 years or longer) even after cells having anergy to the specific antigen induced by an inhibitory factor such as an antibody that can inhibit the interaction between CD80 and/or CD86 and CD28 are eliminated from a subject administered with the anergy induced cells. This means that anergy is newly induced, i.e., infectious immune tolerance is induced, in other cells where anergy can be induced in the body of a subject (recipient) administered with anergy induced cells.

As used herein, "agent" is used broadly and may be any substance or other elements (e.g., light, radiation, heat, electricity, and other forms of energy) as long as the intended objective can be achieved. Examples of such a substance include, but are not limited to, protein, polypeptide, oligopeptide, peptide, polynucleotide, oligonucleotide, nucleotide, nucleic acid (including, for example, DNAs such as cDNA and genomic DNA and RNAs such as mRNA), polysaccharide, oligosaccharide, lipid, organic small molecule (e.g., hormone, ligand, information transmitting substance, other organic small molecule compounds, molecule synthesized by combinatorial chemistry, small molecule that can be used as medicine (e.g., small molecule ligand and the like)), and composite molecule thereof.

As used herein, "inhibitory factor" refers to any type of small molecule, protein, nucleic acid, lipid, saccharide, or like that the can inhibit a given action (e.g., interaction, signaling, or the like). Although not wishing to be bound by a specific theory, anergy is induced in a T cell by blocking the interaction between CD80 and/or CD86 and CD28 on a cell surface to inhibit CD28 costimulation signals in the present disclosure. In the present disclosure, an inhibitory factor used for blocking the interaction between CD80 and/or CD86 and CD28 is selected from the group consisting of a small molecule, protein, nucleic acid, lipid, saccharide, and combination thereof. In one aspect, the protein is an antibody or a variant thereof, or a cell surface molecule or a variant thereof. In another aspect, the variant of the antibody is an antigen binding fragment. In another aspect, the variant of the cell surface molecule is a fusion protein. In another aspect, the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein. In another aspect, the CTLA4-Ig fusion protein is abatacept or belatacept. Combined use of an agent that indirectly inhibits the interaction (e.g., inhibitory factor of an upstream or downstream signal of signaling) is also envisioned.

As used herein, "antibody" broadly refers to a molecule or a group thereof that can specifically bind to a specific epitope on an antigen. As used herein, "antibody" can be broadly a full-length antibody (i.e., antibody with an Fc moiety) or an antibody lacking an Fc moiety. An antibody lacking an Fc moiety only needs to be able to bind to an antigen of interest. Examples of such an antibody include, but are not limited to, Fab antibodies, F(ab')$_2$ antibodies, Fab' antibodies, Fv antibodies, and scFv antibodies, and the like. An antibody can be any type of antibody, i.e., an immunoglobulin known in the art. In an exemplary embodiment, an antibody is an isotype IgA, IgD, IgE, IgG, or IgM class antibody. In an exemplary embodiment, the antibody described herein comprises one or more alpha, delta, epsilon, gamma, and/or mu heavy chains. In an exemplary embodiment, the antibody described herein comprises one or more kappa light chains. In an exemplary embodiment, an antibody is an IgG antibody of one of four human subclasses: IgG1, IgG2, IgG3, and IgG4. Examples of antibodies envisioned to be used in the present disclosure include an antibody derived from an animal of the genus camelidae (e.g., VHH antibody), shark derived antibody (e.g., single stranded antibody), peptibody, nanobody (single domain antibody), minibody, multi-specific antibody (e.g., bispecific antibody, diabody, triabody, tetrabody, tandem di-scFv, tandem tri-scFv), and the like, which are known in the art. See for example Kortt et al., Biomol Eng. 2001 Vol 18: pp 95 to 108, (2001), Todorovska et al., J Immunol Methods. Vol 248: pp 47 to 66, (2001), and the like. Antibodies also include modified and unmodified antibodies. For modified antibodies, an antibody can be bound to various molecules such as polyethylene glycol. A modified antibody can be obtained by applying a chemical modification to an antibody using a known method. See Journal of Japanese Biochemical Society (2016), Vol. 88, No. 3, pp. 380 to 385 for artificially created antibodies and various modification/alteration methods of antibodies.

As used herein, "antibody" narrowly to refers immunoglobulin or a group thereof that can specifically bind to a specific epitope on an antigen. A variant form thereof is referred to as a "variant of an antibody". As used herein, "antibody" can be narrowly a full-length antibody (i.e., antibody with an Fc moiety). A "variant of an antibody" herein can be a variant lacking an Fc moiety of an antibody described above. Therefore, as used herein, an antibody can also be narrowly referred to as a full-length antibody, and a variant of an antibody can also be referred to as a variant of a full-length antibody. A variant lacking an Fc moiety only needs to be able to bind to an antigen of interest. Examples of such a variant include, but are not limited to, Fab antibodies, F(ab')$_2$ antibodies, Fab' antibodies, Fv antibodies, and scFv antibodies, and the like. Variants of an antibody also include modified antibodies and unmodified antibodies. For modified antibodies, an antibody can be bound to various molecules such as polyethylene glycol. A modified antibody can be obtained by applying a chemical modification to an antibody using a known method.

In one embodiment of the present disclosure, "polyclonal antibody" can be generated, for example, by administering an immunogen comprising an antigen of interest to a mammal (e.g., rat, mouse, rabbit, cow, monkey, or the like), avian, or the like to induce the production of a polyclonal antibody specific to an antigen. An immunogen can be administered through one or more immunologic agents, and infusion of an adjuvant when desired. An adjuvant can be used to increase immune responses and can include Freund's adjuvant (complete or incomplete), mineral gel (aluminum hydroxide or the like), surfactant (lysolecithin or the like), or the like. The immunization protocol is known in the art and can be performed by any method that induces an immune response in accordance with the selected host organism ("Tanpakushitsu Jikken Handobukku [*Protein experiment handbook*], Yodosha (2003): 86-91").

In one embodiment of the present disclosure, "monoclonal antibody" encompasses individual antibodies constituting a population that are identical antibodies corresponding to substantially a single epitope, except for antibodies having a mutation that can occur naturally in small amounts. Further, individual antibodies constituting a population may be antibodies that are substantially the same except for antibodies having a mutation that can occur naturally in small amounts. Monoclonal antibodies are highly specific, which are different from common polyclonal antibodies that typically include different antibodies corresponding to different epitopes and/or different antibodies corresponding to the same epitope. In addition to their specificity, monoclonal antibodies are useful in that they can be a hybridoma culture which is not synthesized from contaminated with other immunoglobulins. The description "monoclonal" may indicate a characteristic of being obtained from a substantially homogeneous antibody population. However, such a description does not mean that antibodies must be produced by a specific method. For example, monoclonal antibodies may be prepared by a method similar to the hybridoma method described in "Kohler G, Milstein C., Nature. 1975 Aug. 7; 256 (5517): 495-497". Alternatively, monoclonal antibodies may be prepared by a method similar to the recombinant method described in U.S. Pat. No. 4,816,567. Monoclonal antibodies may also be isolated from a phage antibody library using a method similar to the technology that is described in "Clackson et al., Nature. 1991 Aug. 15; 352 (6336): 624-628." or "Marks et al., J Mol Biol. 1991 Dec. 5; 222 (3): 581-597". Monoclonal antibodies may also be prepared by the method described in "Tanpakushitsu Jikken Handobukku [Protein experiment handbook], Yodosha (2003): 92-96".

In one embodiment of the present disclosure, "chimeric antibody" is, for example, a variable region of an antibody linked to a constant region of an antibody between xenogenic organisms and can be constructed by a genetic engineering technology. A mouse-human chimeric antibody can be prepared by, for example, the method described in "Roguska et al., Proc Natl Acad Sci USA. 1994 Feb. 1; 91 (3): 969-973." For example, the basic method of preparing a mouse-human chimeric antibody links a mouse leader sequence and a variable region sequence in a cloned cDNA with a sequence encoding a human antibody constant region already present in an expression vector of a mammalian cell. After linking the mouse leader sequence and variable region sequence in a cloned cDNA with the sequence encoding a human antibody constant region, the resultant sequence may be linked to a mammalian cell expression vector. A fragment of a human antibody constant region can be from any human antibody H chain constant region and human antibody L chain constant region. Examples of human H chain fragment include Cγ1, Cγ2, Cγ3, and Cγ4, and examples of L chain fragment include Cλ and Ck.

In one embodiment of the invention, "humanized antibody" is, for example, an antibody, which has one or more CDRs derived from a nonhuman species, a framework region (FR) derived from a human immunoglobulin, and a constant region derived from human immunoglobulin and binds to a desired antigen. Antibodies can be humanized using various approaches known in the art (Almagro et al., Front Biosci. 2008 Jan. 1; 13:1619-1633). Examples thereof include CDR grafting (Ozaki et al., Blood. 1999 Jun. 1; 93 (11): 3922-3930.), Re-surfacing (Roguska et al., Proc Natl Acad Sci USA. 1994 Feb. 1; 91 (3): 969-973.), FR shuffle (Damschroder et al., Mol Immunol. 2007 April; 44 (11): 3049-3060. Epub 2007 Jan. 22.) and the like. An amino acid residue of a human FR region may be substituted with a corresponding residue from a CDR donor antibody in order to alter (preferably in order to improve) the antigen bond. The FR substitution can be performed by a method that is well known in the art (Riechmann et al., Nature. 1988 Mar. 24; 332 (6162): 323-327.) For example, an FR residue that is important for antigen binding may be identified by modeling an interaction between a CDR and an FR residue. Further, an abnormal FR residue at a specific position may be identified by sequence comparison.

In one embodiment of the invention, "human antibody" is, for example, an antibody in which a region comprising a variable region and constant region of a heavy chain and variable region and constant region of a light chain constituting the antibody is derived from a gene encoding a human immunoglobulin. Examples of main preparation methods include a method using a transgenic mouse for preparing human antibodies, phage display method, and the like. A method using a transgenic mouse for preparing human antibodies produces human antibodies with diverse antigen binding capabilities instead of mouse antibodies if a functional human Ig gene is introduced into an endogenous Ig knockout mouse. Furthermore, this mouse can be immunized to obtain human monoclonal antibodies by a conventional hybridoma method. This can be prepared, for example, by the method described in "Lonberg et al., Int Rev Immunol. 1995; 13 (1): 65-93." The phage display method is a system that typically expresses an exogenous gene as a fusion protein such that phage infectivity is not lost on the N-terminus side of a coat protein (g3p, g10p, or the like) of fibrous phage such as an *E. coli* virus M13 or T7. Antibodies can be prepared, for example, by the method described in "Vaughan et al., Nat Biotechnol. 1996 March; 14 (3): 309-314".

As used herein, "cell derived from a subject" refers to a cell obtained from a subject administered with the composition of the present disclosure or a cell derived from a cell obtained from the subject. As used herein, "antigen derived from a subject" refers to an antigen produced by a subject themselves which induces an immune response, such as an antigen produced by a subject themselves which causes an autoimmune disease in a subject with the autoimmune disease. As used herein, "antigen that is not derived from a subject" refers to an exogenous antigen that can induce an immune response. As used herein, "antigen-containing material that is not derived from a subject" refers to any substance or collection of substances comprising an antigen that is not derived from a subject. Examples thereof include a cell, cell population, tissue, and the like expressing an antigen that is not derived from a subject.

As used herein, "graft rejection" refers to the immune system of a subject attacking, damaging, or destroying a transplanted organ, tissue, or cell in a subject receiving transplantation of the organ, tissue, or cell.

As used herein, "allergy" refers to a hyperactive immune response to an antigen that is not derived from a subject. An antigen that is not derived from a subject, which induces an allergy, is also referred to as an allergen. Examples thereof include, but are not limited to, tick antigen, egg white antigen, milk antigen, wheat antigen, peanut antigen, soybean antigen, buckwheat antigen, sesame antigen, rice antigen, crustacean antigen, kiwi antigen, apple antigen, banana antigen, peach antigen, tomato antigen, tuna antigen, salmon antigen, mackerel antigen, beef antigen, chicken meat antigen, pork antigen, feline dander antigen, insect antigen, pollen antigen, dog dander antigen, fungal antigen, bacterial antigen, latex, hapten, metal, and the like.

As used herein, "autoimmune disease" refers to any disease in which the immune system exerts an undesirable immune response on its own cell, tissue, or organ. Examples of an autoimmune disease include, but are not limited to, rheumatoid arthritis, multiple sclerosis, type 1 diabetes, inflammatory bowel disease (e.g. Crohn's disease or ulcerative colitis), systemic lupus erythematosus, psoriasis, scleroderma, autoimmune thyroid disease, alopecia areata, Graves' disease, Guillain Barre syndrome, celiac disease, Sjogren's syndrome, rheumatic fever, gastritis, autoimmune atrophic gastritis, autoimmune hepatitis, pancreatitis, ovitis, orchitis, uveitis, lens-induced uveitis, myasthenia gravis, primary myxedema, pernicious anemia, autoimmune hemolytic anemia, Addison's disease, scleroderma, Goodpasture syndrome, nephritis (e.g., glomerulonephritis), psoriasis, pemphigus vulgaris, pemphigoid, sympathetic ophthalmia, idiopathic thrombocytopeniaurpura, idiopathic leukopenia, Wegener's granulomas, and polymyositis/dermatomyositis.

As used herein, "graft-versus-host disease" refers to a transplanted organ, tissue, or cell attacking, damaging, or destroying a cell, tissue, or organ of a subject who received transplantation due to an immune response.

As used herein, "immune rejection caused by transplantation of an iPS cell or ES cell, or a cell, tissue, or organ derived from said cells" refers to an immune rejection resulting from an antigen of an iPS cell or ES cell, or an antigen of a cell, tissue, or organ derived from (differentiated from) an iPS cell or ES cell.

Preferred Embodiments

The preferred embodiments are described hereinafter. It is understood that the embodiments are exemplification of the present disclosure, so that the scope of the present disclosure is not limited to such preferred embodiments. It is understood that those skilled in the art can refer to the following preferred embodiments readily make to modifications or changes within the scope of the present disclosure. Any of these embodiments can be appropriately combined by those skilled in the art by referring to the descriptions herein. It is understood that the following embodiments in the present disclosure can be used alone or as a combination thereof.
(Composition for Eliciting Infectious Immune Tolerance)

The inventors unexpectedly found that immune tolerance persists (infectious immune tolerance), even if a cell formulation comprising cells having anergy induced with an inhibitory factor that inhibits an interaction between CD80/CD86 and CD28 is administered to an organ transplant patient (recipient) and a cell derived from the cell formulation is no longer present in the recipient (no longer detected) in a technology for inducing immune tolerance.

Therefore, in one aspect, disclosure provides a composition for eliciting permanent immune tolerance (infectious immune tolerance) to a donor (antigen derived from a donor or material containing an antigen derived from a donor such as a cell, tissue, or organ of a donor) in a subject, the composition comprising a cell having immune tolerance (anergy) induced by mixing an inhibitory factor that can inhibit an interaction between CD80 and/or CD86 and CD28, a cell derived from the subject, and an antigen derived from the donor or a material containing the antigen. A material containing an antigen can be a cell, which can be irradiated with radiation for preventing the proliferation and activation of the cell.

Once immune tolerance is induced and graft rejection is suppressed, the composition of the present disclosure permanently suppresses or prevents graft rejection without continuous administration of a cell formulation.

In some embodiments, graft rejection is caused by transplanting a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

In a specific embodiment, immune tolerance (anergy) is elicited in a CD4 positive T cell and/or a CD8 positive T cell, and immune tolerance (anergy) is preferably elicited in at least a CD8 positive T cell. Thus, the composition of the present disclosure can comprise a CD4 positive anergic T cell and/or a CD8 positive anergic T cell. The composition of the present disclosure can further comprise a regulatory T cell, such as a FOXP3 positive CD4 positive CD25 positive T cell.

Such an immune tolerance (anergy) elicited cell can be induced by an inhibitory factor such as an antibody that can inhibit the interaction between CD80 and/or CD86 and CD28. Such an inhibitory factor is selected from the group consisting of a small molecule, a protein, a nucleic acid, a lipid, a saccharide, and a combination thereof. In one aspect, the protein is an antibody or a variant thereof, or a cell surface molecule or a variant thereof. In another aspect, the variant of the antibody is an antigen binding fragment. In another aspect, the variant of the cell surface molecule is a fusion protein. In another aspect, the inhibitory factor is selected from the group consisting of an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein. In another aspect, the CTLA4-Ig fusion protein is abatacept or belatacept. In some embodiments, CD80 and/or CD86 are expressed by an antigen presenting cell, and CD28 is expressed by a T cell. In a specific embodiment, an inhibitory factor that can inhibit an interaction between CD80 and/or CD86 and CD28 can be an anti-CD80 antibody and/or an anti-CD86 antibody, or a CTLA4-Ig fusion protein. Examples of inhibitory factors envisioned for use in the present disclosure include a CTLA4-Ig fusion protein as described above. A CTLA4-Ig fusion protein competes with CD28, i.e., a costimulatory receptor on a T cell, for binding to CD80/CD86 on an antigen presenting cell, resulting in functioning to inhibit the activation of T cells. In the present disclosure, abatacept (Orencia®), belatacept, or Maxy-4 is envisioned as the CTLA4-Ig fusion protein. Belatacept comprises two amino acid substitutions (L104E and A29Y) that significantly increase the avidity to bind to CD80 and CD86 (see Davies J K et al., Cell Transplant. (2012); 21 (9): 2047 to 61, Adams A B et al., J Immunol. (2016) 197 (6): 2045 to 50). Examples of inhibitory factors expected to have the same effect as a CTLA4-Ig fusion protein include CD28-Ig fusion protein (see Peach R J et al., J Exp Med. (1994) 180 (6): 2049 to 2058). The inhibitory factor of the present disclosure can also be used in a form of a nucleic acid. In one example, a nucleic acid encoding a CTLA4-Ig fusion protein is envisioned to be introduced into and expressed in a cell via an adenoviral vector or the like. See, for example, Jin Y Z et al., Transplant Proc. (2003); 35 (8): 3156 to 9.
(Therapy)

In another aspect, the present disclosure provides a method of preventing or treating a disease, disorder, or condition in a subject, the method comprising: (1) administering to the subject a formulation comprising a cell having anergy induced by mixing an inhibitory factor such as an antibody that can inhibit an interaction between CD80 and/or CD86 and CD28, a cell derived from the subject, and an antigen derived from the subject or an antigen that is not derived from the subject or a material containing the antigen; and (2) confirming an anergic state of a T cell of the subject, and if an anergic state can be confirmed, performing no additional treatment, and if an anergic state cannot be confirmed, re-administering a formulation comprising the cell.

In this aspect, the present disclosure is a medicament for preventing or treating a disease, disorder, or condition in a subject, wherein the medicament comprises a cell (e.g., T cell) having anergy induced by mixing an inhibitory factor such as an antibody that can inhibit an interaction between CD80 and/or CD86 and CD28, a cell derived from the subject, and an antigen derived from the subject or an antigen that is not derived from the subject or a material containing the antigen, wherein the medicament is characterized by having an anergic state of a T cell of the subject confirmed, and if an anergic state can be confirmed, having no additional treatment performed, and if an anergic state cannot be confirmed, having a formulation comprising the cell re-administered.

In some embodiments, the formulation or medicament comprises a CD4 positive anergic cell, a CD8 positive anergic cell, or a combination thereof. In a specific embodiment, the formulation or medicament comprises a CD8 positive anergic cell.

An anergic state can be confirmed by confirming that a formulation comprising an anergy induced cell is eliminated. Typically, elimination of a formulation comprising an anergy induced cell can be confirmed by obtaining peripheral blood mononuclear cells (PBMCs) from a subject (e.g., recipient) to collect DNA, analyzing MHC that is expressed by a method such as PCR, and detecting the presence/absence of an MHC which is expressed in a cell that is not derived from the subject (e.g., donor derived cell) but is not expressed in the subject (e.g., recipient derived cell). Alternatively, elimination of a formulation comprising an anergy induced cell can be confirmed by labeling the anergy induced cell and detecting the presence/absence of a label in peripheral blood mononuclear cells (PBMCs) from the subject.

In some embodiments, the disease, disorder, or condition is selected from the group consisting of allergy, autoimmune disease, graft-versus-host disease, and immune rejection caused by transplantation of an iPS cell or an ES cell or a cell, tissue, or organ derived therefrom.

In an embodiment where the disease or the like targeted by the present disclosure is graft rejection, an anergic cell can be induced by mixing the inhibitory factor described above, a cell derived from a recipient (PBMC or splenocyte), and an antigen derived a donor or a material containing the antigen derived from a donor. The material containing an antigen derived from a donor can be a PBMC, a splenocyte, or a cell derived from an organ to be transplanted.

In embodiment where the disease or the like targeted by the present disclosure is allergy, an anergic cell can be induced by mixing the inhibitory factor described above, a cell derived from a subject (PBMC or splenocyte), and an allergy-causing antigen that is not derived from a subject.

In embodiment where the disease or the like targeted by the present disclosure is an autoimmune disease, an anergic cell can be induced by mixing the inhibitory factor described above, a cell derived from a subject (PBMC or splenocyte), and an antigen derived from a subject that can be a cause of an autoimmune disease.

In an embodiment where the disease or the like targeted by the present disclosure is a graft-versus-host disease, an anergic cell can be induced by mixing the inhibitory factor described above, a PBMC or splenocyte of a donor providing the graft and recipient derived antigen or a material containing the antigen. The material containing an antigen derived from a recipient can be a PBMC, splenocyte, a cell around a site where an organ is transplanted, or a cell derived therefrom.

In an embodiment where the disease or the like targeted by the present disclosure is immune rejection caused by transplantation of an iPS cell or an ES cell and a cell, tissue, or organ derived from said cells, an anergic cell can be induced by mixing the inhibitory factor described above, a subject derived cell (PBMC or splenocyte), and a cell differentiated from an iPS cell or ES cell used in transplantation.

Therapeutic examples of a disease or the like according to the present disclosure are shown below, but are not limited thereto.

(Allergy and Autoimmune Disease)

In one aspect, the present disclosure provides a method of treating or preventing allergy and/or autoimmune disease using the medicament of the present disclosure and a medicament, composition, or cell mixture used therein. For allergy and autoimmune diseases, a macrophage obtained from the peripheral blood of a patient is differentiated into a dendritic cell (macrophage derived dendritic cell) with high antigen presenting ability by a conventional method. The cell after irradiation of radiation ($\gamma$ rays) is made to present an antigen that is the cause of hyper-reaction in allergy or autoimmune disease, and co-cultured for 1 to 2 weeks with a T cell group contained form the same patient peripheral blood in the presence of an inhibitory factor such as a CTLA4-Ig fusion protein or an anti-CD80 antibody and/or anti-CD86 antibody to obtain an anergic cell that is specific to the antigen causing the allergy or autoimmune disease. The anergic cell is administered to a patient to induce immune tolerance specific to the antigen causing the allergy or autoimmune disease for use in the prevention or treatment of allergy and autoimmune disease. The number of dosings can be multiple, depending on whether the dosing is preventive therapy or treatment, and various conditions such as the severity of symptoms.

(Graft-Versus-Host Disease)

In one aspect, the present disclosure provides a method of treating or preventing graft-versus-host disease using the medicament of the present disclosure and a medicament, composition, or cell mixture used therein. For graft-versus-host disease, in contrast to the treatment of graft rejection, a cell that can be the cause of graft-versus-host disease such as a PBMC or T cell of a donor providing a graft is co-cultured for 1 to 2 weeks with a PBMC derived from a host irradiated with radiation ($\gamma$ rays) or other cells in the presence of an inhibitory factor such as a CTLA4-Ig fusion protein or an anti-CD80 antibody and/or anti-CD86 antibody to obtain an anergic cell that is specific to a host. Administration of such an anergic cell to a host suppresses responses to a host by a graft causing the graft-versus-host disease (and induces immune tolerance) to prevent or treat graft-versus-host disease. The number of dosings can be multiple, depending on whether the dosing is preventive therapy or treatment, and various conditions such as the tissue to be transplanted, the size thereof, or the severity of symptoms.

(Application to Therapy Using an iPS Cell or an ES Cell)

In one aspect, the present disclosure provides a method of treating or preventing immune rejection caused by transplantation of an iPS cell or an ES cell and a cell, tissue, or organ derived said cells or other side effects in the prevention or treatment using an iPS cell or ES cell using the medicament of the present disclosure and a medicament, composition, or cell mixture used therein. Representative examples of target of treatment in the application to treatment using an iPS cell or ES cell include immune rejection caused by transplantation of an iPS cell or an ES cell and a cell, tissue, or organ derived from said cells.

The representative example is described in more detail. In applications to treatment using an iPS cell or ES cell, a dendritic cell or a cell used in transplantation differentiated from an iPS cell or ES cell is irradiated with radiation (γ rays), and the cell is co-cultured for 1 to 2 weeks with a PBMC or T cell group of a patient receiving transplantation in the presence of an inhibitory factor such as a CTLA4-Ig fusion protein or an anti-CD80 antibody and/or anti-CD86 antibody to obtain an anergic cell that is specific to a cell differentiated from an iPS cell or ES cell. Administration of such an anergic cell to a host induces immune tolerance that is specific to an iPS cell or ES cell derived transplanted cell, tissue, and organ and prevent and treat rejection thereto. The number of dosings can be multiple, depending on whether the dosing is preventive therapy or treatment, and various conditions such as the tissue to be transplanted, the size thereof, or the severity of symptoms.

(Allergy)

In one aspect, the present disclosure provides a method of treating or preventing allergy using the medicament of the present disclosure and a medicament, composition, or cell mixture used therein. The inventors demonstrated that a formulation comprising a cell having anergy induced by an inhibitory factor that can inhibit an interaction between CD80/CD86 and CD28 can elicit immune tolerance to allergy. Thus, in another aspect, the present disclosure provides a composition for treating or preventing allergy of a subject, the composition comprising a cell having immune tolerance induced by mixing an inhibitory factor such as an antibody that can inhibit an interaction between CD80 and/or CD86 and CD28, a cell derived from the subject, and an antigen which is a cause of allergy or a material containing the antigen.

In some embodiments, immune tolerance to allergy can be permanent immune tolerance (infectious immune tolerance).

Examples of the antigen which is a cause of allergy include, but are not limited to, food, pollen, drug, and metal, more specifically tick antigen, egg white antigen, milk antigen, wheat antigen, peanut antigen, soybean antigen, buckwheat antigen, sesame antigen, rice antigen, crustacean antigen, kiwi antigen, apple antigen, banana antigen, peach antigen, tomato antigen, tuna antigen, salmon antigen, mackerel antigen, beef antigen, chicken meat antigen, pork antigen, feline dander antigen, insect antigen, pollen antigen, dog dander antigen, fungal antigen, bacterial antigen, latex, hapten, metal, and the like.

(Suppression or Prevention of Immune Rejection Caused by an iPS Cell or the Like)

In one aspect, the present disclosure provides a method of suppressing or preventing immune rejection caused by an iPS cell or the like and a medicament, composition, or cell mixture for the suppression or prevention thereof. The inventors demonstrated that a formulation comprising a cell having anergy induced by an inhibitory factor such as an antibody that can inhibit an interaction between CD80/CD86 and CD28 can elicit immune tolerance to immune rejection caused by an iPS cell or the like or a cell, tissue, or organ derived therefrom. Therefore, in another aspect, the present disclosure provides a composition for suppressing or preventing immune rejection caused by an iPS cell or an ES cell or a cell, tissue, or organ derived therefrom in a subject, the composition comprising a cell having immune tolerance induced by mixing an inhibitory factor such as an antibody that can inhibit an interaction between CD80 and/or CD86 and CD28, a cell derived from the subject, and an antigen derived from the iPS cell or ES cell or a material containing the antigen.

In some embodiments, immune tolerance to immune rejection caused by an iPS cell or the like or a cell, tissue, or organ derived therefrom can be permanent immune tolerance (infectious immune tolerance).

Examples of cell, tissue or organ derived from (differentiated from) an iPS cell or ES cell include, but are not limited to, a nerve cell or tissue, corneal cell or tissue, myocardial cell or tissue, liver or tissue, cartilage cell or tissue, skin cell or tissue, kidney or tissue, and the like. In a preferred embodiment, examples of the cell, tissue, or organ derived from (differentiated from) an iPS cell or ES cell include a nerve cell or tissue, myocardial cell or tissue, cartilage cell or tissue, and skin cell or tissue.

(Method of Manufacturing a T Cell, which is not a Regulatory T Cell, Having Anergy Inducing Activity)

The inventors demonstrated that immune tolerance is induced even if the reactivity of a CD8 positive cell is lost, and a CD4 positive T cell is removed in the post-transplantation late stage (e.g., 80 days or more after the transplantation). Thus, one aspect of the present disclosure provides a T cell having anergy inducing activity, which is not a regulatory T cell. In still another embodiment, the present disclosure provides a method of manufacturing a T cell, which is not a regulatory T cell, having activity to induce anergy to a subject, the method comprising: (A) mixing an inhibitory factor that can inhibit an interaction between CD80 and/or CD86 and CD28, a cell derived from the subject, and an antigen that is not derived from the subject or a material containing the antigen; (B) culturing the mixture to obtain a T cell; and (C) optionally stimulating the T cell with the antigen that is not derived from the subject or the material containing the antigen to confirm that the T cell does not react.

In some embodiments, confirming that the T cell does not react can comprise confirming that the T cell does not proliferate in response to stimulation.

In some embodiments, the T cell comprises a CD4 positive cell and/or a CD8 positive cell. In a specific embodiment, the T cell comprises a CD8 positive cell.

In another aspect, the present disclosure provides a composition for inducing no reaction or a low reaction of a CD8 positive T cell within a subject to a specific antigen.

(Medicament)

In another aspect, the present disclosure provides a medicament for treating or preventing a disease, disorder, or condition caused by an antigen that is not derived from a subject, comprising a cell having immune tolerance induced by mixing an inhibitory factor such as an antibody that can inhibit an interaction between CD80 and/or CD86 and CD28, a cell derived from the subject, and an antigen derived from the subject or an antigen that is not derived from the subject or a material containing the antigen.

In some embodiments, the disease, disorder, or condition treated by the medicament of the present disclosure is selected from the group consisting of graft rejection, allergy, autoimmune disease, graft-versus-host disease, and immune rejection caused by transplantation of an iPS cell or an ES cell or a cell, tissue, or organ derived therefrom.

A typical example of a method of manufacturing and controlling the quality of a cell formulation of the present disclosure is shown hereinafter.

(Manufacture and Quality Control of a Cell Formulation Comprising an Anergic T Cell)

1. Organism Derived Raw Material and Compliance Status Thereof

In one embodiment, an organism derived raw material that is in compliance with the standards for organism derived raw materials described in Table 1 is used in the step of manufacturing an anergic T cell.

An anergic T cell is administered after organ transplantation (e.g., liver transplantation) from a donor to a recipient. A donor organ (e.g., liver) includes donor derived mononuclear cell, which is the material for a self-derived anergic T cell, without removing viruses. A donor organ (e.g., liver) is transplanted into a recipient while including donor derived mononuclear cells. For this reason, a donor derived mononuclear cell used as a material for a self-derived anergic T cell is not considered to fall under an organism derived raw material.

TABLE 1

List of organism derived raw materials

| Name | Contained organism derived raw material Component name | Animal species | Status of compliance to standards for organism derived raw materials |
|---|---|---|---|
| Anti-CD80 antibody | Cell derived component | Chinese hamster (heterologous) | Scheduled to select an antibody manufactured by a step of verifying quality and safety in accordance with ICH-Q5A and ICH-Q5D |
| Anti-CD86 antibody | Cell derived component | Chinese hamster (heterologous) | Scheduled to select an antibody manufactured by a step of verifying quality and safety in accordance with ICH-Q5A and ICH-Q5D |
| ALYS505N-0 | Human serum albumin | Human (autologous) | Selected a pharmaceutical product (plasma fractionated formulation) |
| AIM-V | Human serum albumin | Human (autologous) | Selected a material compatible with the standards for organism derived raw materials *Details described in the master file |
| Human serum albumin | Human serum albumin | Human (autologous) | Selected a pharmaceutical product (plasma fractionated formulation) |

Belatacept (available from, e.g., Bristol-Myers Squibb, New York, NY)

2. Method of Manufacturing a Cell Formulation

In one embodiment, a cell formulation can be manufactured in the following manner. Various numerical values and the like that are exemplified hereinafter are representative examples. Those skilled in the art can manufacture cell formulations by appropriately changing the values or the like.

1) At about 19 days before administration, apheresis is performed on a donor at a medical institution. After the donor apheresis product is irradiated with 30 Gy of radiation to eliminate the ability of cells to proliferate, the product is sent to a cell culture processing facility where the cells are processed.

2) After receiving the donor apheresis product, donor mononuclear cells are separated and collected by density gradient centrifugation, separated into two groups, and stored at −80±10° C. at the cell culture processing facility.

3) At about 14 days before administration, apheresis is performed on a recipient at a medical institution. The recipient apheresis product is sent to a cell culture processing facility where the cells are processed.

4) After receiving the recipient apheresis product, recipient mononuclear cells are separated and collected by density gradient centrifugation, and co-cultured with the thawed donor mononuclear cells and an inhibitory factor such as an anti-CD80 antibody and an anti-CD86 antibody or CTLA4-Ig fusion protein at the cell culture processing facility.

5) The medium is exchanged at about 7 days before administration. The intermediate product cultured for 7 days is collected and co-cultured with the thawed donor mononuclear cells and an inhibitory factor such as an anti-CD80 antibody and an anti-CD86 antibody or CTLA4-Ig fusion protein.

6) The processed cell product is collected by density gradient centrifugation on the day of administration, and then washed and loaded into saline.

7) The product is sent to the medical institution, and administered to the recipient at medical institution.

3. Process Management Test

In one embodiment, the process s management tests described in Table 2 can be performed within the manufacturing steps. Various numerical values and the like and the procedure that are exemplified hereinafter are representative examples. Those skilled in the art can perform a process management test by appropriately changing the values or the like.

TABLE 2

List of process management tests

| Type of test | Tested item | Timing |
|---|---|---|
| Process management test | Cell count | Process management test 1, 2, 3 |
| | Viable cell rate | Process management test 1, 2, 3 |
| | Sterility test | Process management test 1, 2, 4 |
| | Mycoplasma test | Process management test 4 |

4. Specification Test and Characteristic Analysis Test

In one embodiment, the specification test described in Table 3 can be performed using a final product. The procedure exemplified in Table 3 is a representative example. Those skilled in the art can perform the specification test and characteristic analysis test by appropriately changing the procedure. Examples of modified examples thereof include the specification exemplified in Example 11. If the result is not found upon administration of induced suppressor T cells, judgment can be made upon shipping of a clinical trial product by referring to results of a process management test.

The characteristic analysis test described in Table 3 can also be conducted using a cell or final product in the manufacturing process.

TABLE 3

List of final product specification tests

| Item | Tested item | Specification value |
|---|---|---|
| Outer appearance | Outer appearance test | Slightly yellowish white to light yellow cell suspension |
| Cell surface marker | Ratio of CD3⁺ cells | ≥50% |
| | Ratio of CD8⁺ CD44⁺ cells in CD3⁺ cells | ≥10% |
| | Ratio of CD4⁺ CD25⁺ cells in CD3⁺ cells | ≥5% |
| Safety | Sterility test | No growth of microorganism found |
| | Endotoxin | <0.25 EU/mL |
| | Mycoplasma testing | Negative |
| Content | Cell count | ≥1 × 10⁹ cells |
| | Viable cell rate | ≥70% |

The clinical trial product test and characteristic analysis test are described herein. A clinical trial product specification test can comprise the outer appearance, cell count, viable cell ratio, cell surface marker (CD3, CD4, CD8, CD25, CD44, CD45RA/CD45RO), manufacturing process derived impurities (donor derived cell, medium component, anti-CD80 antibody, anti-CD86 antibody, cell freeze damage protection solution component, specific gravity separation solution component), virus test, sterility test, *Mycoplasma* test, and endotoxin. An efficacy test can comprise cytokine production or tritium incorporation test through mixed lymphocyte test (MLR) using cultured cells. The baseline value of cell phenotypes can be, for example for the ratio of CD3 positive cells, typically 50% or greater in the table, or for example 30% or greater, 35% or greater, 40% or greater, 45% or greater, 50% or greater, 55% or greater, 60% or greater, 65% or greater, 70% or greater, or a numerical value therebetween (can be set at a 1% or 0.5% increment or the like). The baseline value of the ratio of CD8 positive CD44 positive cells in CD3 positive cells can be typically 10% or greater in the table, or for example 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The ratio of CD4 positive CD44 positive cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The ratio of CD8 positive CD45RA negative cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, 20% or greater, 25% or greater, 30% or greater, 35% or greater, 40% or greater, or the like. The ratio of CD8 positive CD45RA negative CD45RO positive cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The ratio of CD4 positive CD45RA negative CD45RO positive cells in CD3 positive cells can be undetermined, or the baseline value can be, for example, 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. The baseline value of the ratio of CD4 positive CD25 positive cells in CD3 positive cells can be typically 5% or greater in the table, or for example 1% or greater, 2% or greater, 3% or greater, 4% or greater, 5% or greater, 6% or greater, 7% or greater, 8% or greater, 9% or greater, 10% or greater, 11% or greater, 12% or greater, 13% or greater, 14% or greater, 15% or greater, or the like. For the cell count, 1×10⁹ cells or greater can be used as a representative baseline, or the cell count can be for example, 1×10⁸ cells or greater, 5×10⁸ cells or greater, 1×10⁹ cells or greater, 2×10⁹ cells or greater, 3×10⁹ cells or greater, or the like. For the viable cell ratio, 70% or greater can be used as a representative baseline, or 50% or greater, 55% or greater, 60% or greater, 65% or greater, 70% or greater, 75% or greater, 80% or greater, 85% or greater, 90% or greater, or the like can be used as the baseline.

(Composition of Final Product)

In one example, the final product is comprised of the constituents described in the following table. Those skilled in the art can also appropriately change these specification to change the composition of the prepared regenerative medical product.

TABLE 3-1

List of composition

| Constituent | Composition |
|---|---|
| Self-derived anergic cell | 1 × 10⁹ cells or greater |
| Saline | 100 mL |
| Human serum albumin | 1% |

Those skilled in the art can conduct a specific specification test and characteristic analysis test by applying a change as needed while referring to the technical matters described herein as appropriate.

5. Method of Administering Regenerative Medical Product

In one embodiment, a product is administered once after 14 days from organ transplantation. Those skilled in the art can use a specific administration method, period thereof, and the like by applying a change as needed while referring to the technical matters described herein as appropriate.

(Procedure for Manufacturing Self-Derived Regulatory T Cell)

A typical method of manufacturing a self-derived regulatory T cell is described hereinafter.

Prior Confirmation

In one embodiment, prior confirmation can be performed as described below. Various numerical values, reagents, procedures, and the like exemplified below are representative examples. Those skilled in the art can perform prior confirmation while making appropriate changes.

An infection screening test is administered to a donor and a patient. For the donor, HBs antigen, HCV antibody, HIV-1/2, and HTLV-1 antibody are all confirmed to be negative.

1. Separation of Donor Lymphocyte (Performed Under Aseptic Conditions)

In one embodiment, a donor lymphocyte can be separated in the following matter. Various numerical values, reagents, procedures, and the like exemplified below are representative examples. Those skilled in the art can separate a donor lymphocyte while making appropriate changes.

A donor lymphocyte is collected in a collection bag by apheresis, and radiation is irradiated onto the collection bag.

The radiation irradiated peripheral blood mononuclear cell is placed in a centrifuge tube containing a suitable amount of Ficoll-Paque PREMIUM (GE Healthcare #17-5442-02), Lymphocyte separation Solution (Nacalai Tesque #20828), or the like (e.g., 20 mL), and centrifuged at 860 G for 20 minutes at 22° C. (acceleration of the centrifuge is set to slow, and brake is set to slow).

The supernatant is discarded, and the cell suspension comprising a lymphocyte layer is transferred to another centrifuge tube (e.g., two 50 mL centrifuge tubes).

Saline is added (e.g., suitable amount until the total amount reaches 50 mL) to the centrifuge tube containing the cell suspension. Aspiration and discharge are repeated with a syringe (e.g., 50 ml syringe with an 18 G injection needle) or a pipette for thorough admixing.

The cells are centrifuged at 500 G for 10 minutes at 22° C. (acceleration of the centrifuge can be set to fast, and brake can be set to fast).

The supernatant is discarded. Saline is added again (e.g., suitable amount until the total amount reaches 50 mL). Aspiration and discharge are repeated with a pipette for thorough admixing of a cell pellet.

The cells are centrifuged at 500 G for 5 minutes at 22° C. (acceleration of the centrifuge can be set to fast, and brake can be set to fast).

The supernatant is discarded.

ALYS505N-0 culture (Cell Science & Technology Institute (CSTI) 1020P10) comprising plasma collected from the donor in advance is added to a cell pellet (e.g., suitable amount until the total amount reaches 31 mL). Aspiration and discharge are repeated with a pipette for thorough admixing.

A suitable amount (e.g., 0.3 mL) is withdrawn with a syringe (e.g., 1 mL syringe with an 18 G injection needle) or a pipette to find the cell count and viable cell count.

2. Cryopreservation Donor Lymphocyte (Performed Under Aseptic Conditions)

In one embodiment, a donor lymphocyte can be cryopreserved in the following manner. Various numerical values, reagents, procedures, and the like exemplified below are representative examples. Those skilled in the art can cryopreserve a donor lymphocyte while making appropriate changes.

A freezing bag (e.g., Froze bag F-050, 25 mL freezing bag, Nipro, 89-101) is opened under aseptic conditions, and required information (date, manufacture number, donor name) is written on a label.

A cell suspension is collected with a syringe (e.g., 30 mL syringe with an 18 G injection needle) and placed into the freezing bag.

An ACD solution (Terumo Corporation, TP-A05ACD, e.g., 2 mL to 15 mL of cell suspension) is added to the freezing bag containing the cell suspension. The bag is cooled for about 10 minutes inbetween ice packs cooled to 4° C.

CP-1 (Kyokuto Pharmaceutical Industrial Co., Ltd. 551-27202-4 cell freeze protection solution CP-1, e.g., 8.5 mL) cooled to 4° C. is added to the freezing bag using a syringe (e.g., 20 mL syringe with an 18 G injection needle) over about a minute and a half. The freezing bag is gently stirred at this time.

All air in the freezing bag and the port thereof is withdrawn using a syringe.

The freezing bag is sealed using a tube sealer. The bag is initially cooled for about 5 to 10 minutes at 4° C., and then stored in a −80° C. freezer.

3. Thawing of Donor Lymphocyte (Performed Under Aseptic Conditions)

In one embodiment, a donor lymphocyte is thawed in the following manner. Various numerical values, reagents, procedures, and the like exemplified below are representative examples. Those skilled in the art can thaw a donor lymphocyte while making appropriate changes.

A freezing bag for a stored donor cell is thawed, for example, in a 37° C. thermostatic vessel. The following steps are preferably performed under aseptic conditions.

Cell suspension is withdrawn from the thawed freezing bag using a syringe (e.g., 50 mL syringe with an 18 G injection needle), and transferred to a centrifuge tube (e.g., 12.5 mL each to two 50 mL centrifuge tubes).

For example, 5% albumin solution (Nihon Pharmaceutical Co., Ltd, 123146364, blood donation albumin 5% intravenous injection 12.5 g/250 mL) (e.g., 37.5 mL to 12.5 mL of cell suspension) is added to the centrifuge tube containing the cell suspension and thoroughly admixed. The suspension is then incubated for about 5 minutes.

For example, the cell suspension is centrifuged at 600 G for 10 minutes at 22° C. (e.g., preferably, acceleration of the centrifuge is set to fast, and brake is set to slow).

The supernatant is gently discarded. A cell pellet is suspended by adding a suitable solution such as albumin added saline for washing (e.g., prepared from 25 mL of 5% albumin solution and 19 mL of saline).

For example, the suspension is centrifuged at 600 G for 10 minutes at 22° C. (e.g., preferably, acceleration of the centrifuge is set to fast, and brake is set to slow)

The supernatant is gently discarded. A cell pellet is suspended by adding an ALYS505N culture (e.g., 10 mL to 50 mL centrifuge tube).

Each of an anti-human CD80 antibody (e.g., m2D10.4; Cat. No. 16-0809-85, eBioscience) and anti-human CD86 antibody (e.g., IT2.2; Cat. No. 16-0869-85, eBioscience) is added to a culture bag (e.g., Nipro 87598, Nipro medium ALYS505NB10) containing an ALyS505N-0 culture or a solution equivalent thereto at, for example, a final concentration of 10 μg/mL (or an inhibitory factor such as a CTLA4-Ig fusion protein (e.g., belatacept) is added). To the culture bag, the cell suspension is added by injection with a syringe (e.g., 20 mL syringe with an 18 G injection needle). In one example, the total amount of liquid in the culture bag is about 840 mL.

4. Separation of Patient Lymphocyte to Start of Primary Culture (Performed Under Aseptic Conditions)

In one embodiment, a patient lymphocyte can be separated in the following manner. Various numerical values, reagents, procedures, and the like exemplified below are representative examples. Those skilled in the art can separate a patient lymphocyte while making appropriate changes.

Plasma collected from a patient is heated and inactivated, for example, at 56° C. for 30 minutes in a thermostatic vessel. Plasma that is not immediately used is cryopreserved.

Peripheral blood collected from the patient is placed in a centrifuge tube containing a suitable amount of a suitable medium such as Ficoll-Paque (e.g., 20 mL) and centrifuged for example at 860 G for 20 minutes at 22° C. (preferably, acceleration of the centrifuge is set to slow, and brake is set to slow).

The supernatant is discarded, and the cell suspension comprising a lymphocyte layer is transferred to another centrifuge tube (e.g., two 50 mL centrifuge tubes).

Saline is added (e.g., suitable amount until the total amount reaches 50 mL) to the centrifuge tube containing the cell suspension. Aspiration and discharge are repeated with a pipette for thorough admixing.

For example, the cell suspension is centrifuged at 500 G for 10 minutes at 22° C. (acceleration of the centrifuge can be set to fast, and brake can be set to fast).

The supernatant is discarded. Saline is added again (e.g., suitable amount until the total amount reaches 50 mL). Aspiration and discharge are repeated with a pipette for thorough admixing of a cell pellet.

For example, the cell suspension is centrifuged at 500 G for 5 minutes at 22° C. (acceleration of the centrifuge can be set to fast, and brake can be set to fast).

The supernatant is discarded. The cell pellet is suspended by adding for example ALYS505N-0 culture (e.g., 10 mL) to prepare a cell suspension (e.g., ALYS505N-0 culture is added until reaching a total of 20 mL). At this time, about 0.5 mL of cell suspension is withdrawn to find the cell count, viable cell count, and expression of a surface antigen.

A patient derived inactivated plasma is added to the culture bag containing an inhibitory factor such as an antibody and a donor cell in the ALYS505N-0 culture prepared in "3. Thawing of donor lymphocyte".

The patient derived cell suspension is infused into the culture bag with a syringe (e.g., 20 ml syringe with an 18 G injection needle). The culture bag is sealed using a tube sealer. In one example, the total amount of liquid in the culture bag is about 1000 mL.

Cells are cultured, for example, for 1 week in a 37° C. incubator.

5-1. Medium Exchange (e.g., Performed on Week 1, Preferably Under Aseptic Conditions)

In one embodiment, a medium can be exchanged in the following manner. Various numerical values, reagents, procedures, and like the exemplified below are representative examples. Those skilled in the art can exchange a medium while making appropriate changes.

A culture bag is taken out of an incubator. The content is dispensed in a centrifuge tube (e.g., four 225 mL centrifuge tubes).

For example, the content is centrifuged at 600 G for 10 minutes at 22° C. (e.g., preferably, acceleration of the centrifuge can be set to fast, and brake can be set to fast).

The supernatant is gently discarded. A cell pellet is suspended, for example, by adding an ALYS505N-0 culture to prepare a cell suspension (e.g., add ALyS505N-0 culture until reaching a total of 20 mL). At this time, about 0.3 mL of cell suspension is withdrawn to find the cell count and the viable cell count.

For example, to the culture bag containing ALYS505N-0 culture, the cell suspension is added by injection with a syringe (e.g., 20 ml syringe with an 18 G injection needle).

Each of an anti-human CD80 antibody (e.g., 2D10.4) diluent and anti-human CD86 antibody (e.g., IT2.2) diluent is added to the culture bag by injection with a syringe (e.g., 20 mL syringe with an 18 G injection needle) so that the final concentration would each be for example 10 µg/mL (or an inhibitory factor such as a CTLA4-Ig fusion protein (e.g., belatacept)).

5-2. Donor Lymphocyte Thawing/Antigen Restimulation to Start of Secondary Culture (e.g., Performed on Week 1, Preferably Under Aseptic Conditions)

In one embodiment, donor lymphocyte thawing/antigen restimulation to start of secondary culture can be performed in the following manner. Various numerical values, reagents, procedures, and the like below exemplified are representative examples. Those skilled in the art can perform donor lymphocyte thawing/antigen restimulation to start of secondary culture while making appropriate changes.

A preserved donor cell freezing bag and patient derived inactivated plasma are thawed, for example, in a 37° C. thermostatic vessel. The following steps are preferably performed under aseptic conditions.

Donor cell suspension is withdrawn from the thawed freezing bag using a syringe (e.g., 50 mL syringe with an 18 G injection needle) and transferred to a centrifuge tube (e.g., two 50 mL centrifuge tubes).

A 5% albumin solution (e.g., total of about 50 mL for two 50 mL centrifuge tubes) to the centrifuge tube containing the donor cell suspension and thoroughly admixed. The suspension is then incubated for about 5 minutes.

For example, the suspension is centrifuged at 600 G for 10 minutes at 22° C. (acceleration of the centrifuge is set to fast, and brake is set to slow).

The supernatant is gently discarded. A cell pellet is suspended by adding albumin added saline for washing (e.g., prepared from 25 mL of 5% albumin solution and 19 mL of saline).

For example, the cell suspension is centrifuged at 600 G for 10 minutes at 22° C. (acceleration of the centrifuge is set to fast, and brake is set to slow).

The supernatant is gently discarded. A cell pellet is suspended by adding, for example, an ALYS505N-0 culture (e.g., mL to 50 mL centrifuge tube).

The thawed patient derived inactivated plasma (e.g., 10 mL) is added to the culture bag containing an inhibitory factor such as an antibody and a patient cell in the ALYS505N culture prepared in "3. Thawing of donor lymphocyte" by injection with a syringe (e.g., 20 mL syringe with an 18 G injection needle). Furthermore, the cell suspension described above is added to the culture bag by injection with a syringe (e.g., 20 ml syringe with an 18 G injection needle). In one example, the total amount of liquid in the culture bag is about 1000 mL.

The culture bag is sealed using a tube sealer.

The cells are cultured, for example, for 1 week in a 37° C. incubator.

6. Testing During Secondary Culture (Cultured Cell Withdrawal Test)

In one embodiment, testing during secondary culture can be performed in the following manner. Various numerical values, reagents, procedures, and the like exemplified below are representative examples. Those skilled in the art can perform t during secondary culture while making appropriate changes.

Typically, a small amount of culture is withdrawn from a culture bag and tested for *Mycoplasma* contamination or the like on day 3 from the start of the secondary culture (day 10 of culture).

7. Collection/Loading of Cultured Lymphocyte (Performed Under Aseptic Conditions)

In one embodiment, collection/loading of cultured lymphocyte can be performed in the following manner. Various numerical values, reagents, procedures, and the like exemplified below are representative examples. Those skilled in the art can perform collection/loading of cultured lymphocyte while making appropriate changes.

For example, a culture bag is removed from an incubator on day 7 from the start of the secondary culture (day 14 of culture), and the content is dispensed into a centrifuge tube (e.g., four 225 mL centrifuge tubes).

For example, the content is centrifuged at 600 G for 10 minutes at 22° C. (acceleration of the centrifuge can be set to fast, and brake can be set to fast).

The supernatant is gently discarded. A cell pellet is suspended by adding saline.

For example, the suspension is centrifuged at 600 G for 10 minutes at 22° C. (e.g., preferably, acceleration of the centrifuge can be set to fast, and brake can be set to fast).

The supernatant is gently discarded. A cell pellet is suspended by adding saline (e.g., 10 mL) to prepare a cell suspension.

The cell suspension is gently placed in a centrifuge tube (e.g., 50 mL centrifuge tube) containing a suitable amount of Ficoll-Paque (e.g., 20 mL) as a layer.

For example, the cell suspension is centrifuged at 860 G for 20 minutes at 22° C. (acceleration of the centrifuge is set to slow, and brake is set to slow).

The supernatant is discarded, and the cell suspension comprising a lymphocyte layer is transferred to another centrifuge tube (e.g., 50 mL centrifuge tube).

Saline is added to the centrifuge tube containing the cell suspension (e.g., suitable amount until the total amount of liquid reaches 50 mL). Aspiration and discharge are repeated with a syringe (e.g., 50 ml syringe with an 18 G injection needle) for thorough admixing.

For example, the cell suspension is centrifuged at 500 G for 10 minutes at 22° C. (acceleration of the centrifuge can be set to fast, and brake can be set to fast).

The supernatant is discarded except for about 5 mL. Aspiration and discharge are repeated with a pipette for thorough admixing.

Saline is added (e.g., suitable amount until the total amount of liquid reaches 50 mL). Aspiration and discharge are repeated with a syringe (e.g., 50 mL syringe with an 18 G injection needle) for thorough admixing (a).

For example, the suspension is centrifuged at 500 G for 5 minutes at 22° C. (acceleration of the centrifuge can be set to fast, and brake can be set to fast) (b).

The supernatant is discarded except for about 5 mL. Aspiration and discharge are repeated with a pipette for thorough admixing (c).

(a), (b), and (c) are repeated two more times.

A suitable amount of the supernatant after the final centrifugation is withdrawn (e.g., 4 mL) and subjected to a sterility test and *Mycoplasma* test.

The cells are suspended by adding saline again. The cell suspension is transferred to the final container (e.g., 100 mL saline bottle). A suitable amount (e.g., 4 mL) is withdrawn. The cell count, viable cell count, expression of a surface antigen, and endotoxin content of the final product are studied.

8. Secondary Packaging

In one embodiment, secondary packaging can be performed in the following manner. Various numerical values, reagents, procedures, and like below the exemplified are representative examples. Those skilled in the art can perform secondary packaging while making appropriate changes.

Typically, a subject ID, manufacture number, and expiration date are entered and printed on a label based on a suitable standard (typically NUHCPC-M-12-ATREG) and the label is applied to a container.

"Dosage and Administration, indication, and precaution for use or handling" is specified based on a suitable standard (typically NUHCPC-PMF-ATREG14).

The tested material and "Dosage and Administration, indication, and precaution for use or handling" are placed in a resealable plastic bag.

The bag is stored within a monitoring unit in a transport container until shipping.

(Note)

As used herein, "or" is used when "at least one or more" of the listed matters in the sentence can be employed. When explicitly described herein as "within the range of two values", the range also includes the two values themselves.

Reference literatures such as scientific literatures, patents, and patent applications herein cited are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

The present disclosure is more specifically described hereinafter based on the Examples. However, the present disclosure is not limited to the Examples. Throughout the entire application, all of the cited references are directly incorporated herein by reference.

Example 1: Immune Tolerance Induction Experiment

This Example tested whether direct contact of a cell formulation administered to elicit immune tolerance with a responder cell to be reacted is required for the exertion of suppression action. The methodology is described hereinafter.

(Non-Contact Mixed Culture)

(Materials and Methods)

(Preparation of Anergic Cells)

The experiment depicted in FIG. 1 was conducted in accordance with a method already described in a reference (1-4). Briefly, mononuclear cells (PBMC) were separated from human peripheral blood of 4 volunteers (2 were designated as stimulators and 2 were designated as responders) using Promo cell's Lymphocyte separation Media (Cat. No. C-44010), Ficoll-Paque PREMIUM (GE Healthcare #17-5442-02), Lymphocyte separation Solution (Nacalai Tesque #20828), or the like, and adjusted with a 2% human type AB serum (pooled) added Biowest ALYS505N-0 medium (Cell Science & Technology Institute (CSTI)

1020P10) so that the concentration would be 4×10⁶ cells/ml. Stimulator PBMCs were irradiated with 30 Gy of radiation (γ ray) and mixed with responder PBMCs at 1:1. To the mixed PBMCs, eBioscience's mouse anti-human CD80 antibodies (2D10.4) (Cat. No. 16-0809-85) and mouse anti-human CD86 antibodies (IT2.2) (Cat. No. 16-0869-85) were added so that the final concentration would each be 10 μg/mL, and culture was started in a 37° C. 5% $CO_2$ incubator on a 12-well plate (Corning, #3513) (1 to 2.5 ml), 6-well plate (Corning, Cat. No. 3516) (3 to 6 ml), 6 cm petri dish (Greiner CELLSTAR® dish, Cat. No. 628160) (3 to 6 ml), or 10 cm petri dish (Corning, Cat. No. 430167) (10 to 15 ml) (day 0). After removing the culture by centrifugation on day 5 from the start of the culture, a culture comprising anti-CD80 antibodies/anti-CD86 antibodies and radiation irradiated stimulator PBMCs were added under the same condition as the start of the culture. The cells were collected 2 days later (day 7), and the culture was washed out by centrifugation to obtain anergic cells.

(Culture (Double Chamber Culture) Using a Cell Culture Insert Plate (Cat. N: PSHT004R1) Having a Cell Non-Permeable Membrane (Millicell®)

The obtained anergic cells or responder PBMCs were adjusted to a ratio of 1:1 with radiation irradiated stimulator PMBCs and cultured in the top row well having a membrane generally known as transwell membrane through which a humoral factor permeates, but cells cannot permeate. In the bottom row, newly collected responder PBMCs and radiation irradiated stimulator PBMCs were mixed at 1:1, each at 2×10⁶ cells/mL (4 well each at final concentration of about 200 μL). These top row and bottom row wells were assembled on a 96-well plate (Corning, Cat. No. 3381) and cultured in a 37° C. 5% $CO_2$ incubator.

On day 4 from starting the culture, ³H-thymidine (10 μL) was added. On day 5 from starting the culture (after 16 to 20 hours from addition of ³H-thymidine), cultured cells were harvested with a Cell Harvester (Molecular Devices). The amount of ³H-thymidine incorporation was measured with a scintillation counter.

(Results)

The results are shown in the right panel of FIG. 1.

Since the top row and the bottom row are separated by a transwell membrane, culture using such a configuration limits intracellular contact within the wells in each row, but produced humoral factors can move between wells. When anergic cells are placed in the same row as stimulator cells/responder cells (right end), the proliferative reaction of responder cells due to stimulator cell stimulation seen on the left end is suppressed. In contrast, when anergic cells and stimulator cells were placed in the top row, the suppression effect is significantly diminished (second from the right), suggesting that involvement of immunosuppressive cytokines (IL-10 or the like) is low. When fresh responder cells and stimulator cells were placed in the top row (second from the left), slight increase in proliferation was observed. This is inferred as an effect of a humoral factor such as IL-2 that induces cell proliferation produced by a reaction in the top row. The results demonstrated that anergic cells, to exert immunosuppression ability, require direct contact with naïve responder cells in addition to contact with stimulator cells, and exertion of suppression ability requires antigen stimulation culture in the presence of anti-CD80/86 antibodies for inducing anergy.

Example 2: Mouse Experiments Showing the Effect of Adoptive Transfer of Ex Vivo Induced Anergic Cells in Mouse Heart Transplantation and Persistence of Immune Tolerance Even after the Cells are Eliminated This Example demonstrated that immune tolerance persists even after cells derived from a cell formulation are no longer present. The procedure thereof is described hereinafter.

(Materials and Methods)

The methods and materials that were used in this Example are described below.

The experiment was conducted in accordance with a method already described in a reference (5 to 7). Briefly, spleens were extracted from C57BL6 (hereinafter B6) mice and BALB/c mice that were genetically engineered to express GFP, and red blood cells were subjected to hemolysis to obtain splenocytes (lymphocytes), which were then adjusted in an RPMI 1640 medium (Sigma; R8758-500MK) comprising 10% inactivated fetal bovine serum (FCS) (SIGMA #172012-500ML Lot 11D257 or biosera #FB-1380/500 Lot. 015BS482) so that the concentration would be 4×10⁶ cells/ml. The stimulator BALB/c splenocytes were irradiated with 30 Gy of radiation (Y ray) and then mixed with B6 splenocytes at 1:1. The cells were cultured for 14 days in a 37° C. 5% $CO_2$ incubator in a 12-well plate (Corning, #3513) (1 to 2.5 mL), 6-well plate (Corning, Cat. No. 3516) (3 to 6 mL), 6 cm Petri dish (Greiner CELLSTAR® dish, Cat. No. 628160) (3 to 6 mL), or 10 cm petri dish (Corning, Cat. No. 430167) (10 to 15 mL) after adding eBioscience's hamster anti-mouse CD80 antibody (16-10A1) (Cat. No. 16-0801-82) and rat anti-mouse CD86 antibody (GL1) (Cat. No. 14-0862-82) so that each final concentration would be 10 μg/mL. After removing the culture by centrifugation on day 7 from starting the culture, a culture comprising a BALB/c radiation irradiated splenocyte and anti-CD80 antibodies/anti-CD86 antibodies was newly added under the same condition as that at the start of culture. After 14 days, cells were collected to obtain anergic cells.

6×10⁶, 4×10⁶, or 2×10⁶ GFP expressing B6 mouse derived anergic cells were administered from the caudal vein of a wild-type B6 mouse transplanted with a heart of a BALB/c mouse after three days from irradiation of 2 Gy of radiation to observe rejection of the heart. A recipient mouse infused with 6×10⁶ anergic cells after 3 months or more from the transplantation was slaughtered to obtain peripheral blood mononuclear cells (PBMCs) as well as extracted spleen, lymph node, and lymphocytes from the transplanted heart. The presence of infused anergic cells was studied through fluorescence of GFP using flow cytometry. The same analysis was performed using a B6 recipient mouse infused with 6×10⁶ anergic cells and transplanted with a heart of a syngenic B6 mouse. Further, 3 days, 7 days, 28 days, 50 days, and 100 days after transplanting the BALB/c mouse heart, a heart transplanted recipient mouse infused with 6×10⁶ anergic cells was slaughtered to obtain peripheral blood mononuclear cells (PBMCs) as well as extracted spleen, lymph node, and lymphocytes from the transplanted heart. After extracting a genomic gene therefrom, the presence of anergic cells infused with a GFP gene by a method with higher sensitivity than amplification by PCR was studied.

(Results)

Figure 2:
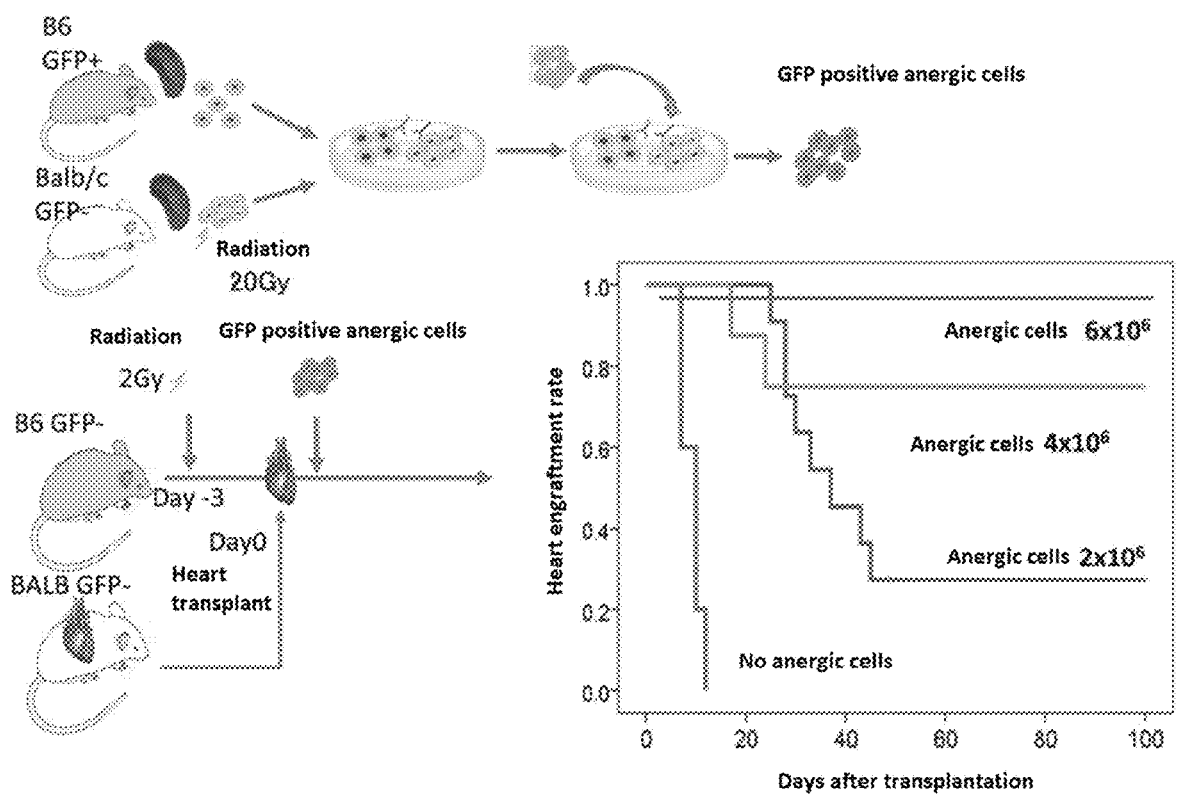
FIG. 2 is an experimental result showing that immune tolerance persists even if there is no longer a cell derived from a cell formulation in a recipient.
Figure 2:
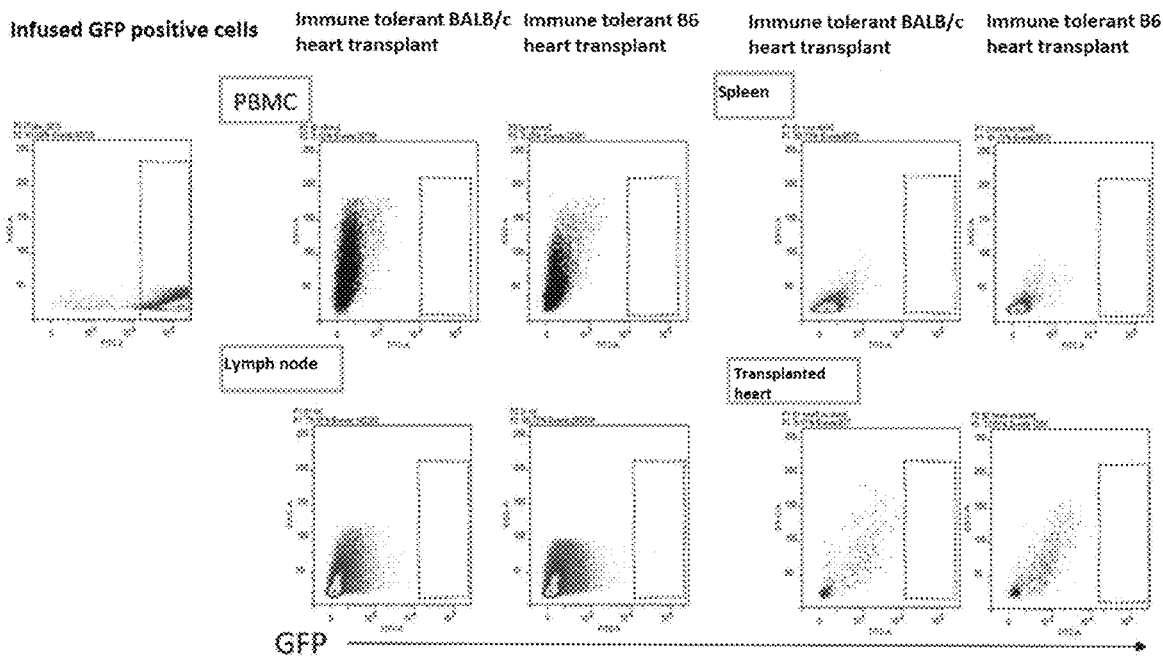
Figure 3:
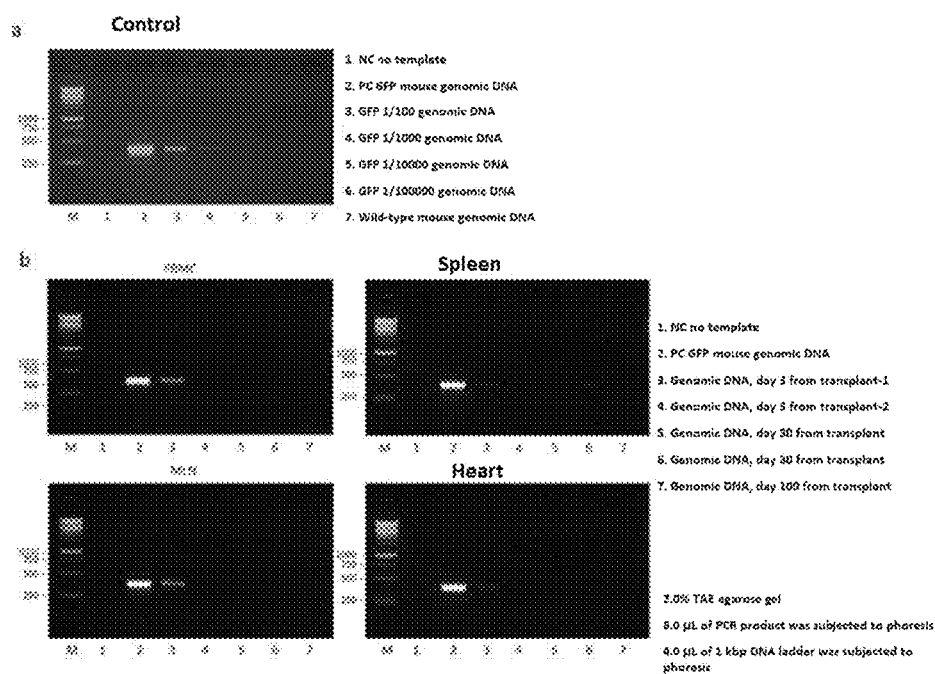
FIG. 3 shows that immune tolerance persists, even after cells from a cell formulation are no longer in a recipient, by using a detection methodology with higher sensitivity than amplification of a GFP gene in a genomic gene by PCR.

The results are shown in FIGS. 2 and 3. As shown in FIG. 2a, the engraftment rate of transplanted heart improved by infusion of anergic cells in a cell count dependent fashion. Survival of a transplanted heart of 100 days or longer was observed in all mice from infusion of 6×10⁶ anergic cells, i.e., induction of immune tolerance to the transplanted heart was observed. However, as shown in FIG. 2b, the infused anergic cells were undetected by expression of fluorescence not only in the peripheral blood, lymph node, and spleen, but also the transplanted heart. As shown in FIG. 3b, expression of a GFP gene was able to be confirmed in all of peripheral blood, spleen, mesenteric membrane lymph node, and transplanted heart up to 3 days after transplantation, but the expression of the gene was not detected in any of the tissues from 7 days after transplantation, even with a detection methodology with higher sensitivity than amplification of a GFP gene in the genomic gene by PCR, which is capable of detection at 0.1% (presence of 1/1000 diluted GFP mouse genomic DNA: lane 4) as shown in FIG. 3a. This suggests that survival (immune tolerance) of a transplanted heart for 100 days or longer from donor specific immunosuppression by infusion of anergic cells is induced, but the infused cells are eliminated within the recipient body within a week.

Example 3: Immunosuppression by Anergic Cells is Antigen Specific

Figure 4:
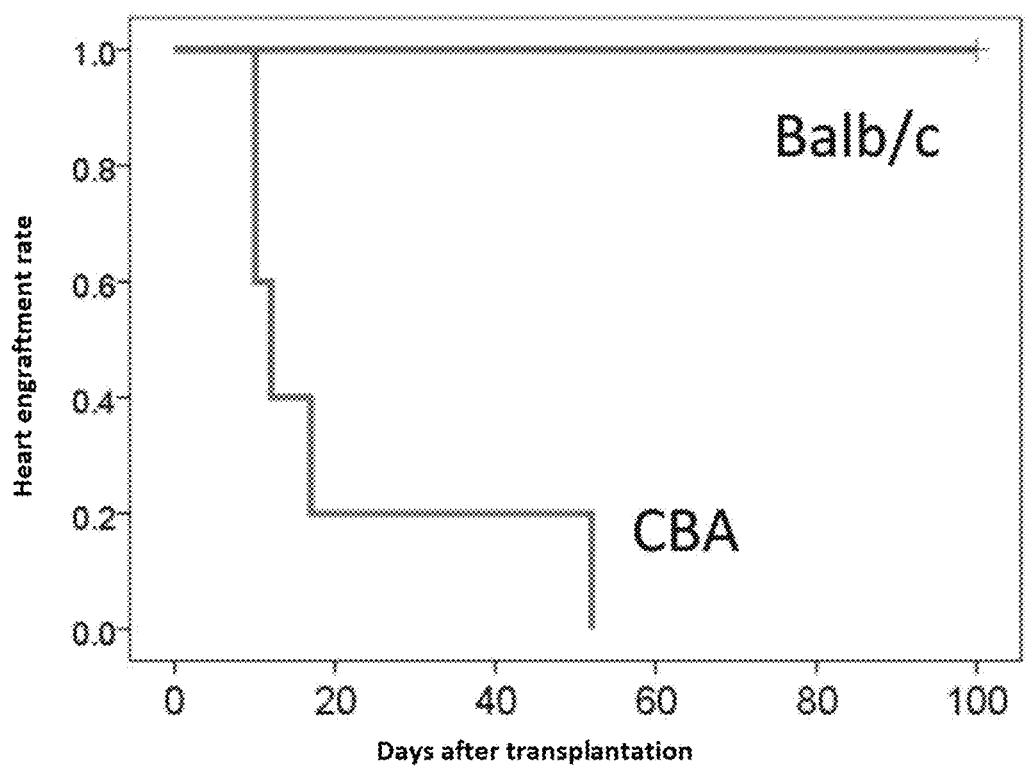
FIG. 4 is a diagram showing that immunosuppression by anergic cells is antigen specific.

This Example demonstrated that anergic cells have specificity and do not suppress rejection against an antigen derived from a third party.
(Materials and Methods)
Anergic cells were obtained by stimulating splenocytes obtained from wild-type B6 mice (H-2b) with splenocytes derived from BALB/c mice (H-2b) in the presence of anti-CD80/86 antibodies by the same approach as Example 2. 5×10⁶ anergic cells were administered to wild-type B6 mice transplanted with a heart of a BALB/c mouse or CBA mouse (H-2$^k$) three days after irradiation of 2 Gy of radiation from the caudal vein to observe rejection of the heart.
(Results)
As shown in FIG. 4, infusion of anergic cells derived from a B6 mouse stimulated with Balb/C mouse splenocytes in the presence of anti-CD80/86 antibodies into a B6 mouse inhibited rejection of the transplanted heart of the BALB/c mouse 100%. The heart was surviving even after 100 days. In contrast, 3rd party CBA mouse hearts quickly induced rejection after transplantation and were rejected 100% at about 50 days. This shows that lymphocytes derived from a recipient reacted with an antigen in the presence of anti-CD80/86 antibodies have an ability to suppress immune responses in a stimulating antigen specific manner.

Example 4: Experiment Showing Infectious Immune Tolerance

Figure 5:
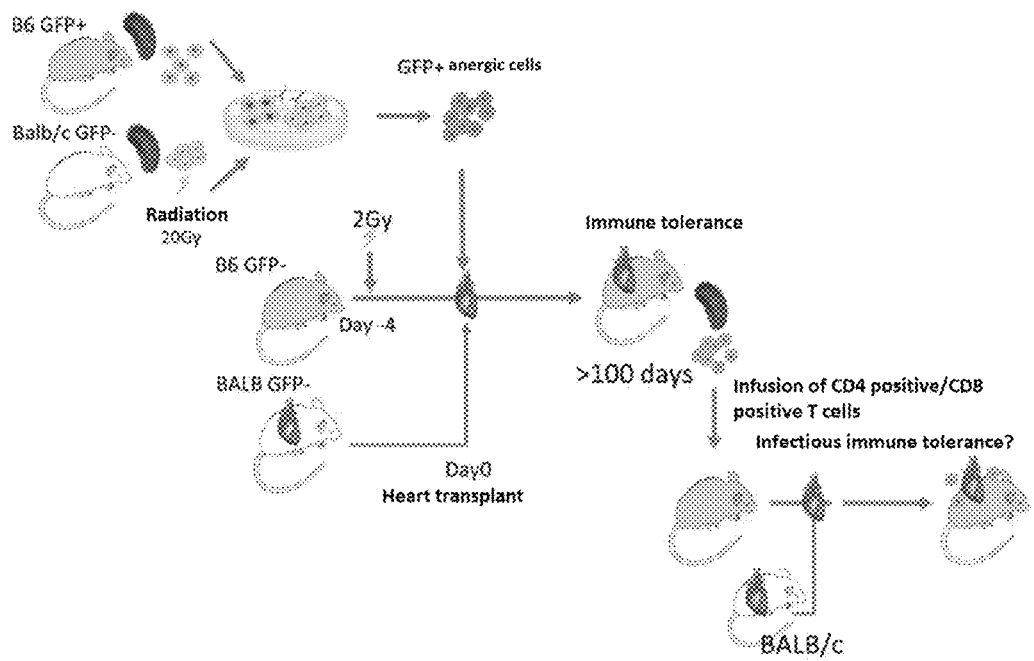
FIG. 5 shows an experiment showing infectious immune tolerance performed in Example 4.
Figure 6:
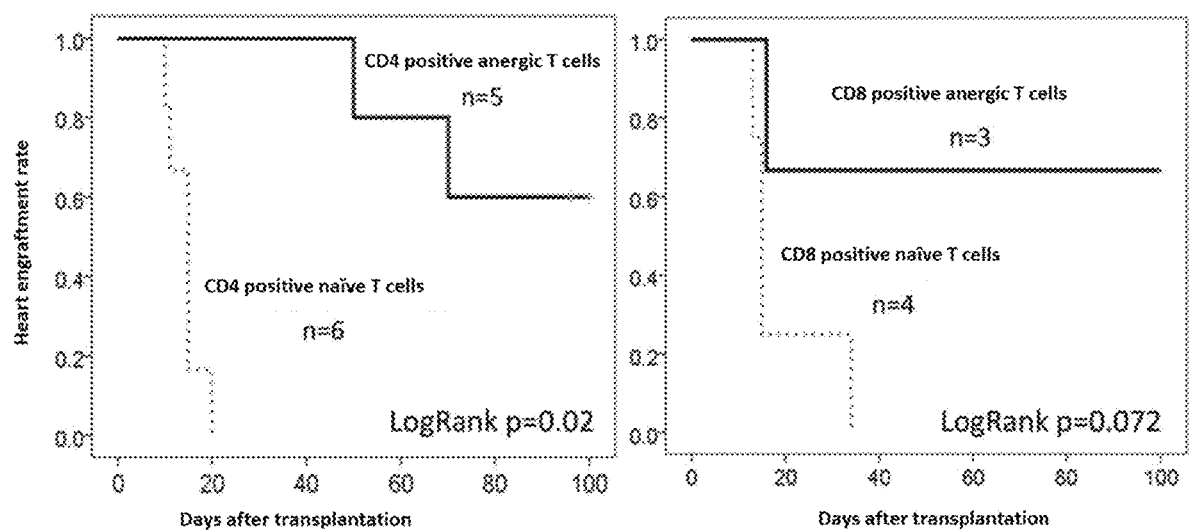
FIG. 6 shows results of the infectious immune tolerance shown in FIG. 5. The left panel shows the engraftment rate (immune tolerance) from infusion of CD4 positive T cells obtained from a mouse immune tolerance to a transplanted heart induced by infusion of anergic cells. The right panel shows the engraftment rate (immune tolerance) from infusion of CD8 positive T cells obtained from a mouse having immune tolerance to a transplanted heart induced by infusion of anergic cells.

This Example demonstrated that infectious immune tolerance is induced.
(Materials and Methods)
The experiment depicted in FIG. 5 was conducted after obtaining anergic cells by the same approach as Example 2. Briefly, anergic cells were obtained by stimulating splenocytes obtained from B6 mice that were genetically engineered for all cells to express fluorescent dye GFP with radiation irradiated splenocytes derived from BALB/c mice in the presence of anti-CD80/86 antibodies. 5×10⁶ anergic cells were administered to wild-type B6 mice transplanted with a heart of a BALB/c mouse 4 days after irradiation of 2 Gy of radiation from the caudal vein. After 100 days or more from transplantation a heart deemed to have immune tolerance induced, a recipient mouse was slaughtered to extract the spleen, then red blood cells were subjected to hemolysis to obtain splenocytes. The anergic cells were separated into recipient mouse derived GFP negative CD8 positive or GFP negative CD4 positive cells using a CD8-T cell isolation kit (BioLegend 480035) or CD4-T cell isolation kit (BioLegend 480033). Likewise, CD8 positive or CD4 positive cells were also collected from fresh (naïve) splenocytes newly obtained from a B6 mouse. 4×10⁶ of the isolated cells were administered to a wild-type B6 mouse transplanted with a heart of a BALB/c mouse 4 days after irradiation of 2 Gy of radiation from the caudal vein to observe rejection of the heart.
(Results)
The results are shown in FIG. 6.
Infusion of CD4 positive T cells or CD8 positive T cells obtained from a mouse having immune tolerance to a transplanted heart induced by infusion of anergic cells induced immune tolerance to the transplanted heart in about 60% of recipient mice. In contrast, infusion of the same number of naïve CD8 positive T cells or CD4 positive T cells could not induce immune tolerance, and the transplanted heart was rejected in all cases. These results show that cells capable of inducing anergy in the body of a recipient mouse are newly induced by infusion of anergic cells obtained by in vitro culture, i.e., infectious immune tolerance is induced. As shown in FIG. 1, it is inferred that the induction rate of immune tolerance can be increased by increasing the infused cell count.

Example 5: Infusion of Subculture of Allo Specific Suppressive Anergic Cells in a Human In Vitro Model This Example demonstrated that infusion of subculture of allo specific suppressive anergic cells in a human in vitro model also has an effect.
(Materials and Methods)
Human derived anergic cells were obtained by the same approach as Example 1 (1-4). Briefly, mononuclear cells (PBMC) were separated from human peripheral blood of 4 (2 were designated as stimulators and 2 were volunteers designated as responders) using Promo cell's Lymphocyte separation Media (Cat. No. C-44010), and adjusted with a 2% human type AB serum (pooled) added Biowest ALYS505N-0 medium so that the concentration would be 4×10⁶ cells/ml. Stimulator PBMCs were irradiated with 30 Gy of radiation and mixed with responder PBMCs at 1:1. To the mixed PBMCs, eBioscience's mouse anti-human CD80 antibodies (Cat. No. 16-0809-85) and mouse anti-human CD86 antibodies (Cat. No. 16-0869-85) were added so that the final concentration would each be 10 μg/mL, and culture was started in a 37° C. 5% $CO_2$ incubator on a 12-well plate (Corning, #3513), 6-well plate (Corning, Cat. No. 3516), 6 cm petri dish (Greiner CELLSTAR® dish, Cat. No. 628160), or 10 cm petri dish (Greiner CELLSTAR® dish, Cat. No. 664 160-013) (day 0). After removing the culture by centrifugation on day 5 from starting the culture, a culture comprising anti-CD80 antibodies/anti-CD86 antibodies and radiation irradiated stimulator PBMCs was added under the same condition as the start of the culture. The cells were collected 2 days later (day 7), and the culture was washed out by centrifugation to obtain anergic cells (1$^{st}$). The cells were labeled with a fluorescent dye CFSE.
CFSE labeled cells using a CFSE cell proliferation kit (Invitrogen C34554) were mixed so that the ratio with respect to the newly collected identical responder PBMCs would be 1:1, and then added to a mixed culture system of radiation irradiated identical stimulator PBMCs and responder cells at 1:1 (day 7). On day 4 of the culture (day 11), radiation irradiated stimulator PBMCs were re-supplemented. On day 7 of the culture (day 14), only CFSE negative responder derived cells were collected by sorting using JSAN (Bay bioscience Co., Ltd.) ($2^{nd}$ anergic cells). The cells were labeled with CFSE, mixed with newly collected identical responder PBMCs so that the ratio would be 1:1 therewith, and added to a mixed culture system of radiation irradiated identical stimulator PBMCs and responder cells at 1:1 (day 14). On day 4 of the culture (day 18), radiation irradiated stimulator PBMCs were re-supplemented. On day 7 of the culture (day 21), CFSE negative responder derived cells were collected by sorting using JSAN ($3^{rd}$ anergic cells).

(Evaluation of Immunosuppression Ability)

On day 2 after culture in each mixed culture system, CFSE negative responder CD4 positive cells were isolated by sorting. IL-2 and IL-10 expression, mRNA levels were analyzed by quantitative real-time PCR (qPCR) (TaqMan™).

The $1^{st}$ anergic cells and $2^{nd}$ anergic cells were collected on their respective last day of induction, and diluted so that the ratio with respect to responder PBMCs would be 1:1 to 1:0.125. The cells were added to a mixed culture system (4 well each at $2\times10^5/200$ µL/well) in a 96-well plate (Corning, Cat. No. 3799) comprising responder PBMCs and newly collected identical stimulator derived PBMCs irradiated with 30 Gy of radiation (γ ray) at a cell count of about 1:1, and cultured in a 37° C. 5% $CO_2$ incubator. On day 4 from starting the culture, $^3$H-thymidine (10 µL) was added. On day 5 from starting the culture (after 16 to 20 hours from addition of $^3$H-thymidine), cultured cells were harvested with a Cell Harvester (Molecular Devices). The amount of $^3$H-thymidine incorporation was measured with a scintillation counter.

(Results)

Figure 7:
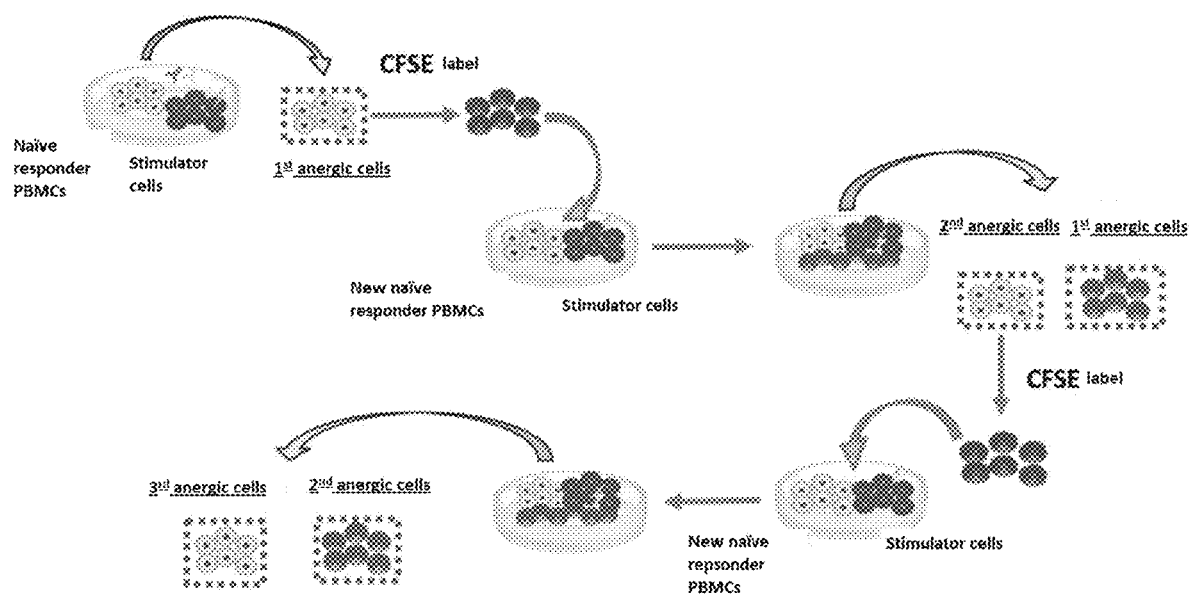
FIG. 7 shows the methodology of infusion of allo specific suppressive anergic cell subculture in a human in vitro model performed in Example 5.
Figure 8A:
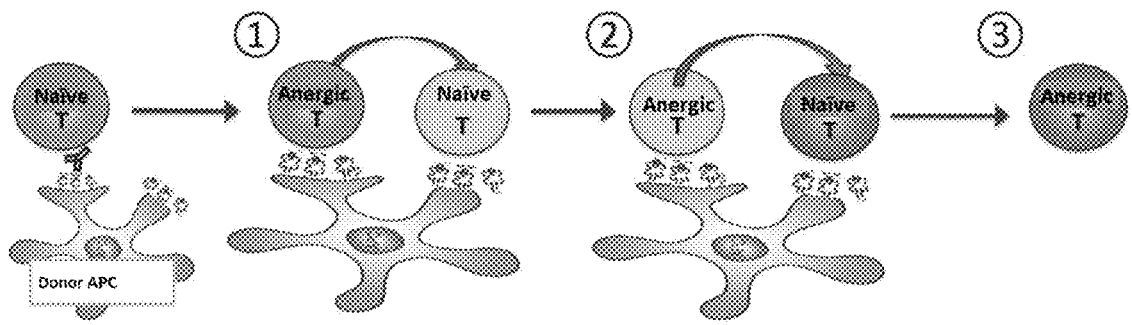
FIG. 8a shows a schematic diagram thereof.

In this experiment depicted in FIG. 7, a reaction such as those depicted in the schematic diagram of FIG. 8a is assumed to be taking place in vitro. It is understood that an immunosuppression ability is imparted to a naïve cell reacted in the presence of an anergic cell by this mechanism.

Figure 8B:
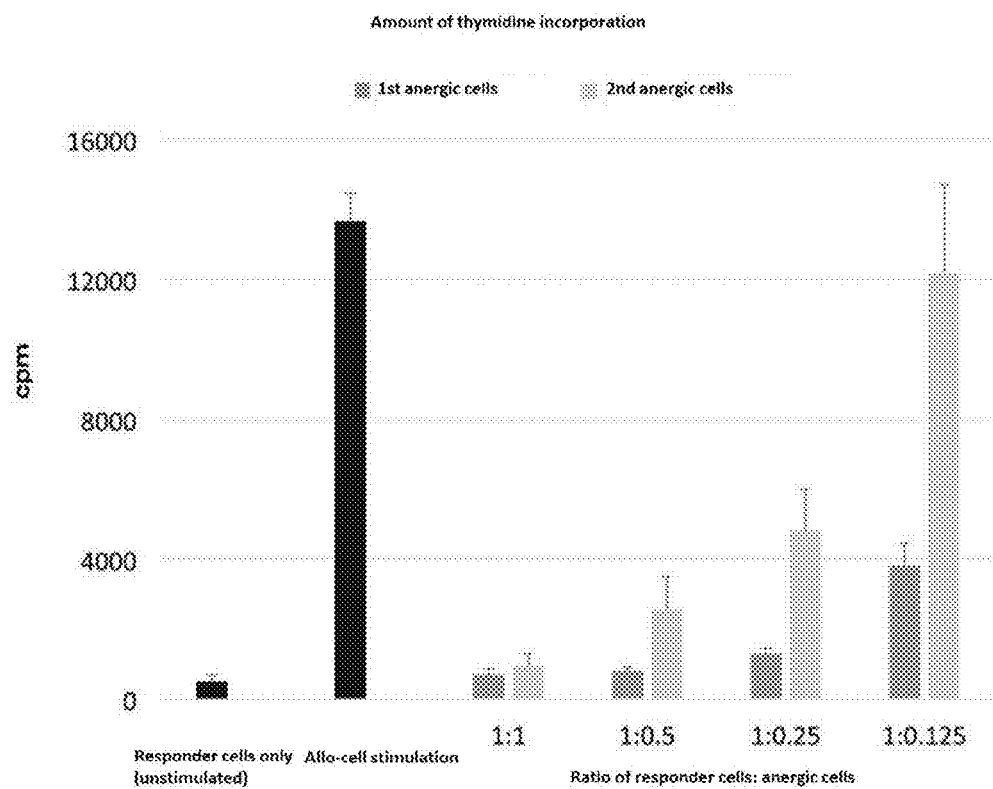
FIG. 8b shows the CPM value of the amount of $^3$H-thymidine incorporation. The graph shows, from the left, CPM values for naïve responder cells only, under stimulation by allo cells, and cases where anergic cells were added to naïve responder cells at a ratio of responder cells:anergic cells of 1:1, 1:0.5, 1:0.25, and 1:0.125.
Figure 8C:
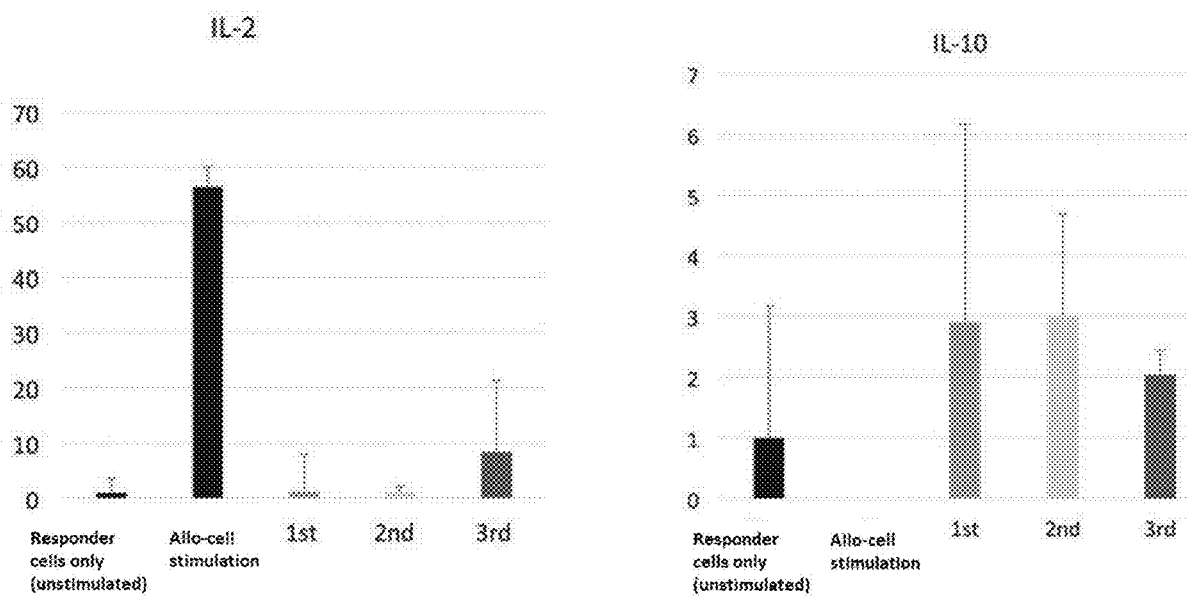
FIG. 8c shows the production of IL-2 (left) and IL-10 (right). Each graph shows, from the left, naïve responder cells only, stimulation by allo cells of CD4 positive naïve cells, stimulation by allo cells of CD4 positive naïve cells upon addition of $1^{st}$ anergic cells, stimulation by allo cells of CD4 positive naïve cells upon addition of $2^{nd}$ anergic cells, and stimulation by allo cells of CD4 positive naïve cells upon addition of 3rd anergic cells. It was demonstrated that each of the 1st anergic cells, 2nd anergic cells, and 3rd anergic cells suppressed the production of cytokine IL-2 that induces cell proliferation from responder CD4 positive cells, while inducing the production of representative cytokine IL-10 that suppresses immune responses. Each graph shows the ratio when the amount of production of each cytokine under the condition of only responder cells (no stimulation) is assumed to be 1.

FIG. 8b shows the CPM value of the amount of $^3$H-thymidine incorporation, indicating that the $1^{st}$ anergic cells and $2^{nd}$ anergic cells exert an immunosuppression ability. FIG. 8c shows that the $1^{st}$ anergic cells, $2^{nd}$ anergic cells, and $3^{rd}$ anergic cells all suppress the production of cytokine IL-2, which induces cell proliferation from responder CD4 positive cells, but induce the production of representative cytokine IL-10 that suppresses immune responses. This indicates that the $1^{st}$ anergic cells, $2^{nd}$ anergic cells, and $3^{rd}$ anergic cells all have immunosuppressive action. The above results show that the immunosuppression ability due to anergic cells is passed onto naïve cells having response to the same antigen stimulation in the presence of the anergic cells suppressed, i.e., infectious immunosuppression ability is passed on even to human immune cells.

Example 6: Confirmation of Reactivity of CD8 Positive Cells and Necessity of CD4 Positive T Cells This Example confirmed that immune tolerance is induced even if the reactivity of a CD8 positive cell is lost, and a CD4 positive T cell is removed in the post-transplantation late stage (80 days or later) in mice.

(Materials and Methods)

The procedure and the material used in this Example are described hereinafter.

Anergic cells were obtained by stimulating splenocytes obtained from a wild-type B6 mouse with BALB/c cells in the presence of anti-CD80/86 antibodies by the same approach as Example 2. $5\times10^6$ of these anergic cells were administered to a wild-type B6 mouse transplanted with a heart of a BALB/c mouse 3 days after irradiation of 2 Gy of radiation from the caudal vein. For 3 to 24 days, 25 to 42 days, or 80 to 100 days post heart transplantation, 200 µg of an anti-mouse CD4 antibody (GK 1.5) prepared in a laboratory for removing CD4 positive T cells including reg T cells was intraperitoneally administered every 3 days. The rejection of the transplanted heart was observed.

(Results)

Figure 9:
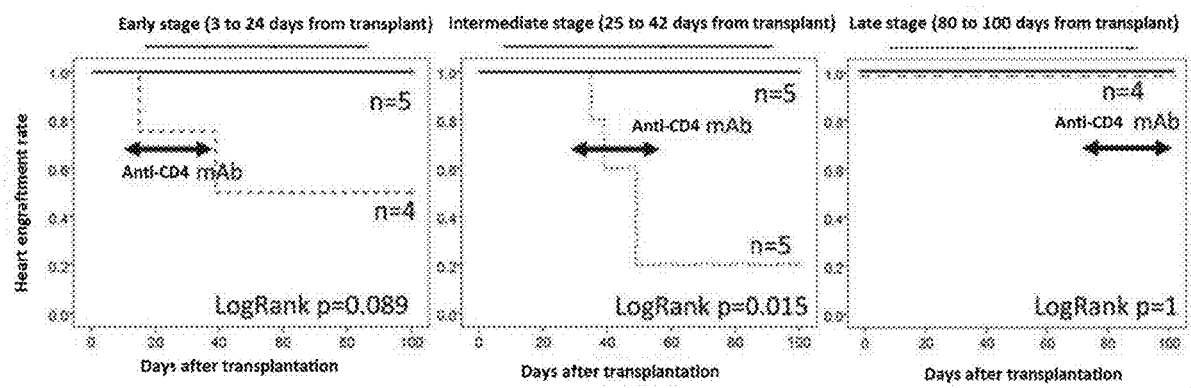
FIG. 9 shows results of testing reactivity of CD8 positive cells and the necessity of CD4 positive T cells. The figure shows the engraftment rate of the transplanted heart (ratio of no rejection of the heart) when CD4 positive cells including regulatory T cells (also denoted as reg T cells herein) were removed with anti-CD4 antibodies in, from the left, the early stage (3 to 24 days), intermediate stage (25 to 42 days), and late stage (80 to 100 days), respectively.

The results are shown in FIG. 9. When CD4 positive cells including reg T cells were removed with an anti-CD4 antibody in the early stage (3 to 24 days) or intermediate stage (25 to 42 days) post-heart transplantation, mice rejecting the transplanted heart were observed. In contrast, when CD4 positive cells including reg T cells were removed in the late stage (80 to 100 days), rejection of the transplanted heart was not observed in any of the mice. In other words, CD4 positive T cells including reg T cells are required for immune tolerance up to about 42 days, and depletion thereof induces rejection of the transplanted heart due to CD8 positive T cells. However, after 80 days, CD4 positive T cells including reg T cells is no longer required, suggesting that the reactivity of CD8 positive cells is itself lost. Specifically, it is shown that immune tolerance is ultimately induced without any immunosuppressive cell (after 80 days) in a recipient who has undergone cell therapy.

Example 7: Reaction of CD8 Positive T Cell to a Donor

This Example studied the reaction of a CD8 positive T cell to a donor.

(Materials and Methods)

Figure 10A:
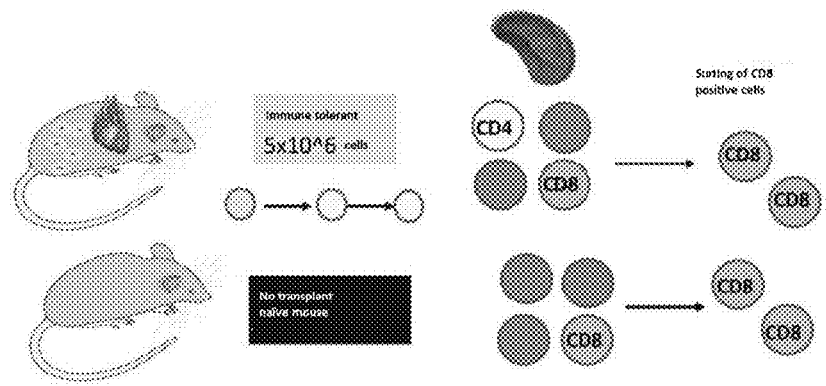
FIG. 10a shows the procedure of an experiment showing the reaction of CD8 positive T cells to a donor.
Figure 10B:
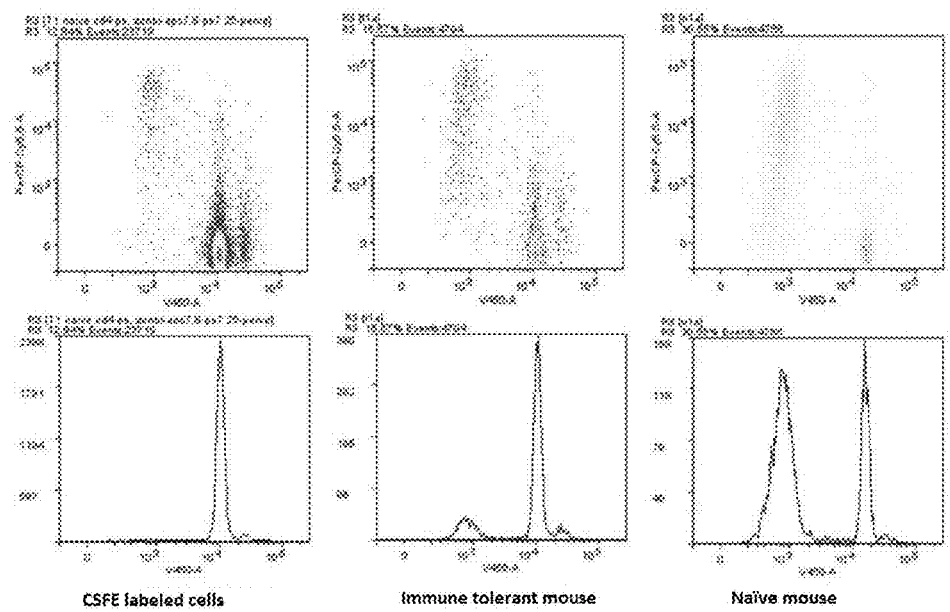
FIG. 10b is the result of mixing and culturing the cells labeled with CSFE with BALB/c derived radiation irradiated splenocytes at 2×10⁶ cells/mL at 1:1 in a 12-well plate (Corning, Cat. No. 3513) or a 24-well plate (Corning, Cat. No. 3526) and investigating the expression of CSFE of the CD8 positive T cells on day 5 of culture by flow cytometer (BD verse). The figure shows, from the left, donor cells, immune tolerant mouse, and naïve mouse. The top row shows results in dot plot, and the bottom row shows results in a histogram.

Anergic cells were obtained by stimulating splenocytes obtained from a wild-type B6 mouse with BALB/c cells in the presence of anti-CD80/86 antibodies by the same approach as Example 2. $5\times10^6$ of these anergic cells were administered to a wild-type B6 mouse transplanted with a heart of a BALB/c mouse 3 days after irradiation of 2 Gy of radiation from the caudal vein. Splenocytes were obtained from naïve mice and immune tolerance induced mice with no rejection observed and a transplanted heart that has survived for 100 days or longer, and were labeled with CSFE using a CFSE cell proliferation kit (Invitrogen C34554) (FIG. 10a). The cells labeled with CSFE were mixed with BALB/c derived radiation irradiated splenocytes at 1:1 at $2\times10^6$ cells/mL in a 12-well plate (Corning, Cat. No. 3513) or a 24-well plate (Corning, Cat. No. 3526), and cultured. The expression of CSFE in CD8 positive T cells on day 5 of culture was studied with a flow cytometer (BD verse) (FIG. 10b).

Figure 10C:
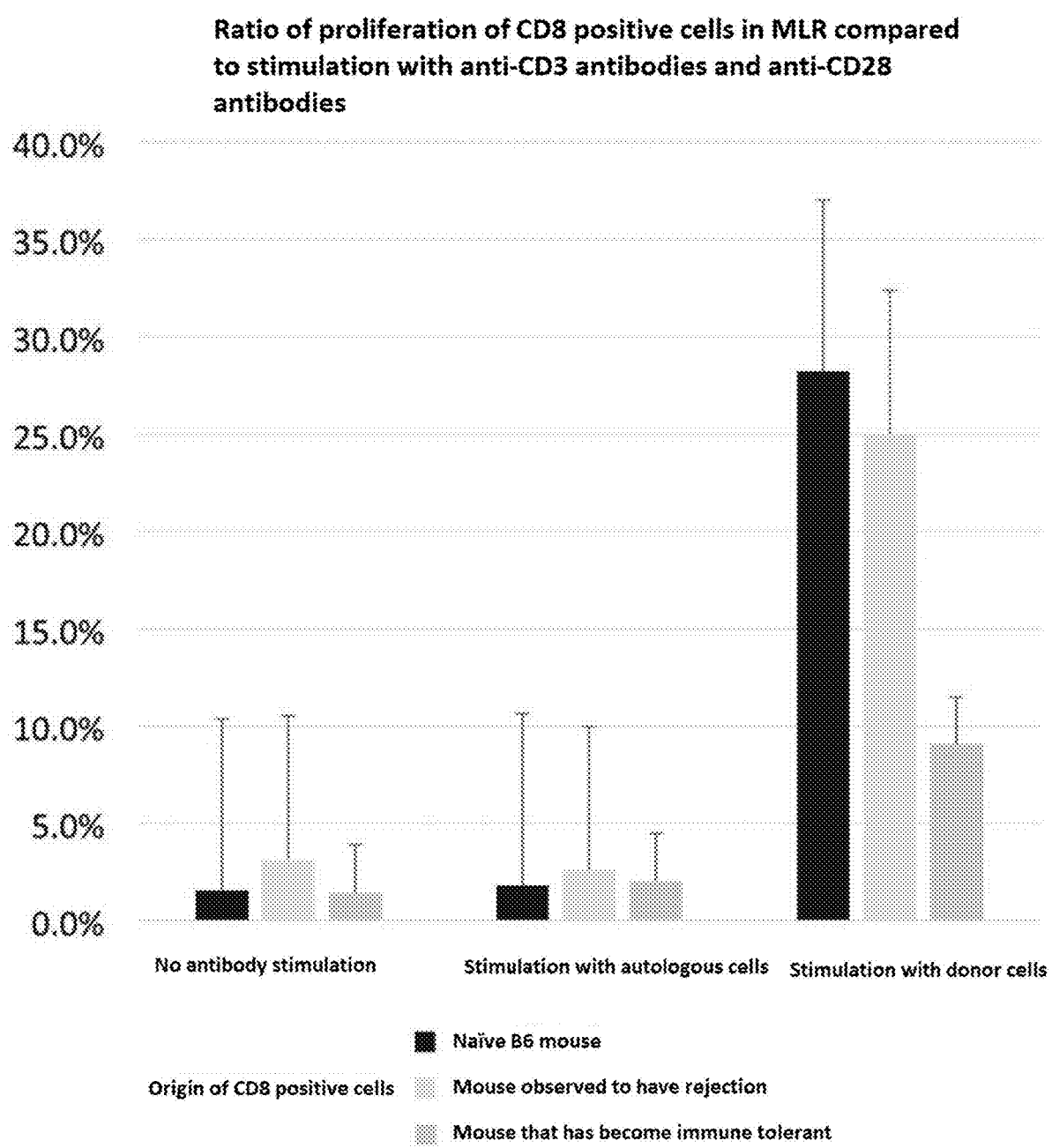
FIG. 10c shows a comparison of CD8 MLR proliferation ratio compared to anti-CD3/CD28 antibody stimulation. In the graph, the left group is the result for no anti-CD3/CD28 antibody stimulation, the middle group is the result for stimulation with radiation irradiated autologous cells, and the right group is the result for stimulation with radiation irradiated donor cells. In each group, the bars indicate a reaction of, from the left, CD8 positive T cells of naïve B6 cells, CD8 positive T cells derived from a mouse that has rejected a transplanted heart, and CD8 positive T cells of an immune tolerant mouse.

Furthermore, splenocytes of immune tolerance induced mice (mice having immune tolerance induced by administration of $4\times10^6$ anergic cells), rejection mice (mice observed to have rejection from insufficient administration of $2\times10^6$ anergic cells), and wild-type mice without transplantation were reacted with PE fluorescence labeled anti-mouse CD8 antibodies (53-6.7; eBioscience, #12-0081-85), and then CD8 positive cells were separated with auto-MACS (Miltenyi Biotech) using anti-PE magnetic beads (Miltenyi Biotec #1300-10-639). The cells were mixed with B6 and BALB/c mouse derived radiation irradiated splenocytes each at 1×10⁶ cells/mL at 1:1 on a 96-well plate (Corning, Cat. No. 3799), and cultured (culture volume of 200 μL). On day 4 from starting the culture, ³H-thymidine (10 μL) was added. On day 5 from starting the culture (after 16 to 20 hours from addition of ³H-thymidine), cultured cells were harvested with a Cell Harvester (Molecular Devices). The amount of ³H-thymidine incorporation was measured with a scintillation counter. An experiment was conducted to induce proliferation of all CD8 positive T cells by stimulation with anti-CD3 antibodies (eBioscience #MA5-17622) and anti-CD28 antibodies (eBioscience #16-0281-82) as positive control (direct addition of 10 μg each to the culture system or pre-coating the culture plate). The decrease in the ability to proliferate was studied by comparison (%) therewith (FIG. 10c).

(Results)

The results are shown in FIG. 10.

As shown in FIG. 10b, the expression level of CSFE decreased in many naïve CD8 positive T cells by dividing (proliferating) due to stimulation of donor cells (right), but there is no cell for which the CSFE fluorescence level decreases because naïve cells alone do not proliferation (left). In contrast, CD8 positive T cells of a mouse having immune tolerance elicited hardly undergo a division (proliferation) response even with stimulation of donor cells, so that there are few cells with reduced CSFE expression (middle). Specifically, CD8 positive cells alone inherently respond to donor cells, but CD8 positive cells of a mouse having immune tolerance induced have lost reactivity by themselves. In other words, immune tolerance (unresponsiveness) of CD8 positive T cell independent of the presence of suppressor cells is induced.

As shown in FIG. 10c, the proliferative response to donor stimulation, compared to anti-CD3/anti-CD28 antibody stimulation, was reduced for CD8 positive T cells of a mouse having immune tolerance induced relative to CD8 positive T cells of a naïve mouse or CD8 positive T cells of a mouse observed to have rejection against a transplanted heart. This indicates that cells that antigen-specifically respond and proliferate are reduced in all CD8 positive T cells. This shows the possibility of induction of donor antigen specific T cell specific clone anergy or clone removal in mice having anergy induced.

The above results of elimination of cells infused as cell therapy in one week and experimental results showing that immune tolerance is also induced by cells of a mouse having immune tolerance induced exhibiting infectious immune tolerance demonstrate that infectious immune tolerance is elicited by the present disclosure.

The following conclusions are reached in view of the above results.

1. The anergic cells of the present disclosure exert an immunosuppression ability by contacting a naïve cell of a recipient.
2. Infused suppressive anergic T cells become undetectable.
3. New cells with an immunosuppression ability are induced in the body of the recipient by the infused suppressive anergic cells.
4. Ultimately, the reactivity of donor antigen specific CD8 positive clones decreases significantly. This indicates the possibility of the induction of clone anergy or clone removal. Thus, it is suggested that infused donor specific anergic cells are eliminated in the early stage from the body of the recipient, but continue to induce, even after their elimination, new donor specific immunosuppressive cells in the body of the recipient and ultimately cause donor specific CD8 positive T cells themselves, which play a central role in graft rejection, to lose the reactivity.

Therefore, it is understood from the results of this Example that infused suppressive anergic T cells becoming undetectable and/or new cells with an immunosuppression ability being induced in the body of a recipient are useful for the management of therapy using the present disclosure. It is also understood that detection of a donor antigen specific CD8 positive clone can be utilized in managing whether treatment is excellent.

Example 8: Immune Tolerance in Allergic Pneumonia (Asthma) Model

This Example demonstrated whether immune tolerance is induced in an allergic pneumonia (asthma) model.

(Materials and Methods)

Figure 11:
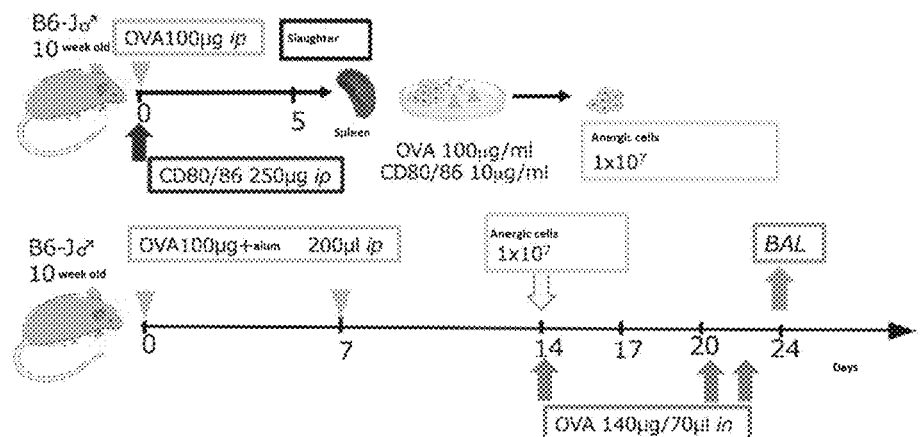
FIG. 11 shows the procedure of immune tolerance in an allergic pneumonia (asthma) model shown in Example 8.

As shown in FIG. 11, an experiment was conducted using an allergic pneumonia (asthma) model already described in a reference (8).

(Obtaining OVA Specific Anergic Cells)

B6 mice sensitized to OVA by concurrent intraperitoneal administration of 100 μg of OVA (Sigma-Aldrich #01641, MBL Life Science TS-5001-P, or the like) and 250 μg of each of anti-mouse CD80/86 antibodies were slaughtered after 5 days to extract the spleen, and splenocytes were obtained by hemolysis. The splenocytes were adjusted in an RPMI 1640 medium comprising 10% FCS so that the concentration would be 4×10⁶ cells/mL. 100 μg/mL of OVA and each of CD80/86 antibodies were added thereto so that the final concentration would be 10 μg/mL. The splenocyte suspension was cultured for 7 days in a 37° C. 5% $CO_2$ incubator to obtain OVA specific anergic cells.

Evaluation of Suppression Ability in an Allergy (Rhinitis) Model

A model which administers 70 μL of PBS comprising 140 μg of OVA on day 14, 17, and 20 as a nasal drip to a mouse sensitized to OVA by intraperitoneal administration of 100 μg of OVA and alum adjuvant containing emulsion on day 0 and day 7 was used as an allergic pneumonia (asthma) model. 1×10⁷ induced anergic cells were administered on day 14 from the caudal vein. On day 24, Bronchoalveolar Lavage (BAL) was collected from washing the trachea using 1 ml of saline. The number of white blood cells (CD45 positive cells) and eosinophils (calculated as a ratio of CD45 positive CD11b positive Siglec F positive cells in CD45 positive cells) that seeped out thereto was counted. In addition, IL-4 in BAL was measured by ELISA (eBioscience #88-704-88).

(Results)

Figure 12:
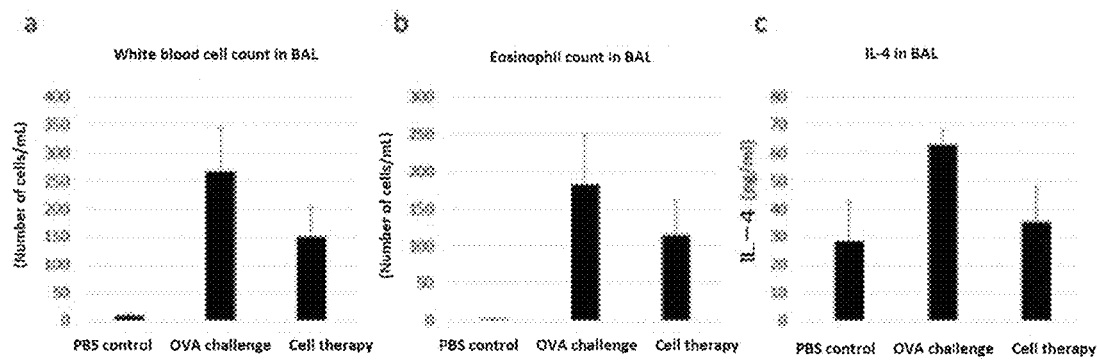
FIG. 12 shows experimental results of immune tolerance in the allergic pneumonia (asthma) model shown in FIG. 11.

The results are shown in FIG. 12. FIG. 12a shows the number of white blood cells contained in the bronchial effusion (BAL), and FIG. 12b shows the number of eosinophils contained in BAL. The number of white blood cells and eosinophils seeping out decreased due to the infusion of anergic cells. Furthermore, as shown in FIG. 12c, IL-4, which is considered to be involved with allergic reactions, contained in the BAL, also decreased. This shows that infusion of anergic cells induced by co-culture with anti-CD80/86 antibodies and OVA induces immune tolerance and diminishes allergic reactions in an allergic pneumonia (asthma) model using OVA.

Example 9: Elicitation of Immune Tolerance in Food Allergy Model

This Example studied the elicitation of immune tolerance in a food allergy model.

The details are described hereinafter.

(Materials and Methods)

Figure 13:
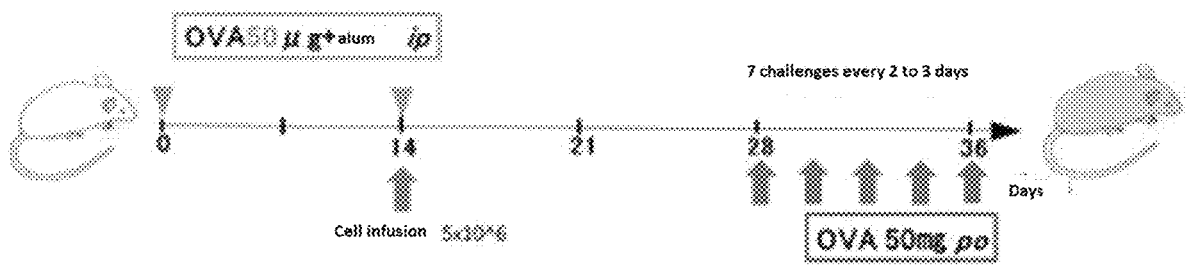
FIG. 13 shows the procedure of immune tolerance elicitation in the food allergy model shown in Example 9.

As depicted in FIG. 13, an experiment was conducted using the food allergy model already described in a reference (9) was conducted. Briefly, $5 \times 10^6$ anergic cells obtained by the same method as Example 8 were administered on day 14 to a food allergy model induced by oral administration of 50 mg of OVA 7 times every 2 to 3 days from day 28 from the caudal vein to a mouse sensitized to OVA by intraperitoneal administration of 100 µg of OVA and alum adjuvant (Thermo Fisher #77161) containing emulsion on day 0 and 14. The mouse was slaughtered after 36 days to harvest the intestinal tract. The reg T cells in the intestinal tract were stained by immunostaining using biotin labeled anti-FoxP3 antibodies (eBioscience #13-5773-829), Alexa 594 labeled streptavidin (Molecular Probes #S11227), and FITC labeled anti-CD4 antibodies (RM4-5, Molecular Probes #553047), and eosinophil (eosin intense stain cells) in the intestinal tract was stained by HE staining. For the CD4 positive Foxp3 positive cell density, fluorescent immunostaining images were obtained with a CCD camera AxioCam HRc (Zeiss) through a fluorescence microscope Axioplan 2 imaging (Zeiss), and then the area of the subject of measurement was measured and positive cells in said area was counted using image analysis software KS400 (Zeiss) to calculate the positive cell count/mm². For the eosinophil density, HE (hematoxylin-eosin) staining images were obtained with a CCD camera AxioCam MRc (Zeiss) through an optical microscope Axioskop 2 plus (Zeiss), and then the area of the subject of measurement was measured and eosin strong positive eosinophils in said area was counted using image analysis software KS400 (Zeiss) to calculate the positive cell count/mm².

(Results)

Figure 14:
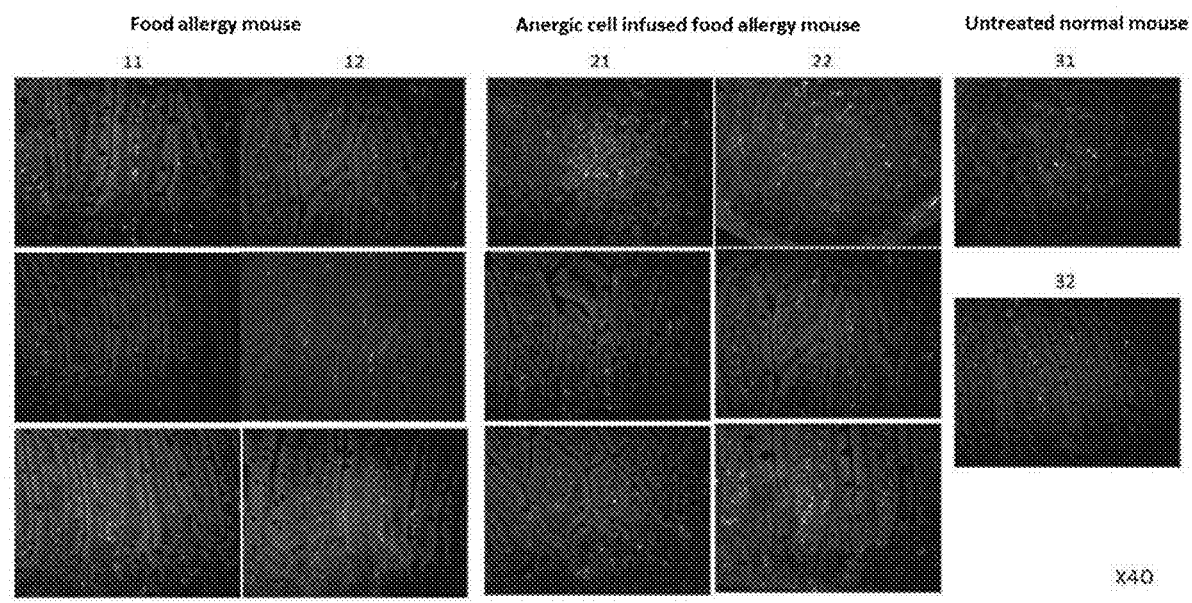
FIG. 14 shows results of typical immunofluorescent staining using intestinal tract FoxP3/CD4 as a result of eliciting immune tolerance in the food allergy model shown in FIG. 13. The left panel (two columns) shows results of two (11, 12) food allergy induced mice (food allergy mice), the middle panel (two columns) shows results of two (21, 22) mice subjected to induction of food allergy and infusion of anergic cells (anergic cell infused food allergy mice), and the right end shows results of two (31, 32) normal mice (untreated normal mice). Independent images of tissue staining at 3 sites in food allergy mice and anergic cell infused food allergy cell infused mice (three vertically arranged images).
Figure 15A:
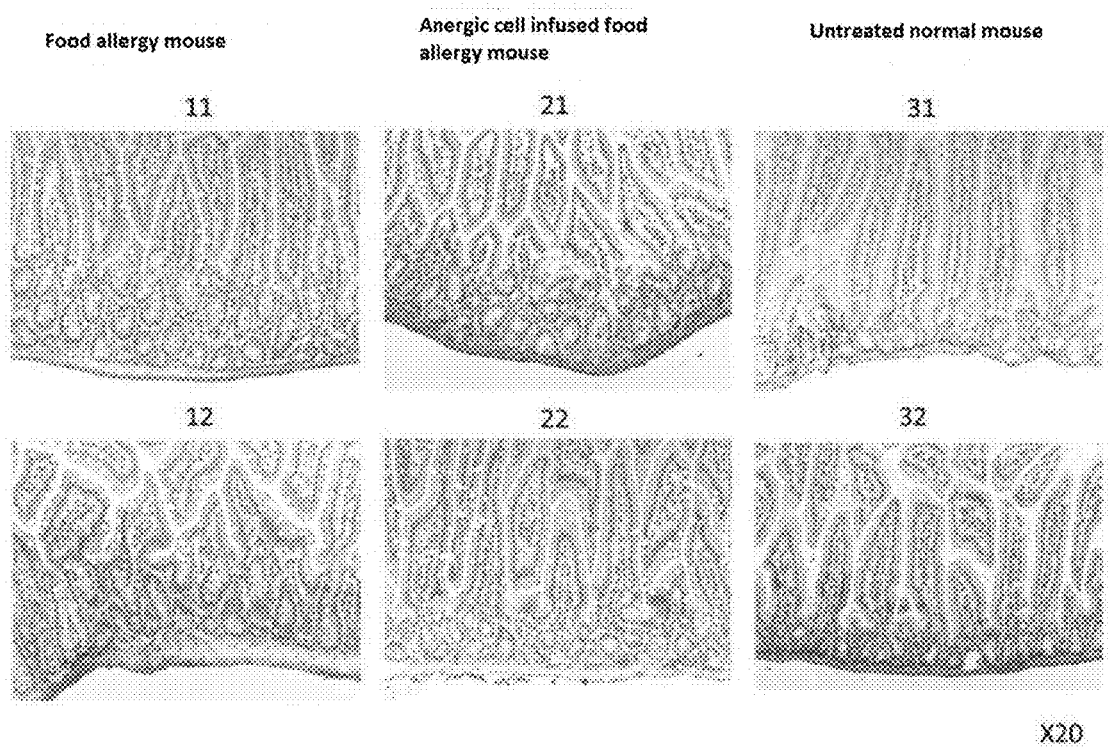
FIG. 15a shows typical pictures of HE staining of an intestine in each mouse (mice 11 and 12 (food allergy mice), 21 and 22 (anergic cell infused food allergy mice), and 31 and 32 (untreated normal mice) in FIG. 14).
Figure 15B:
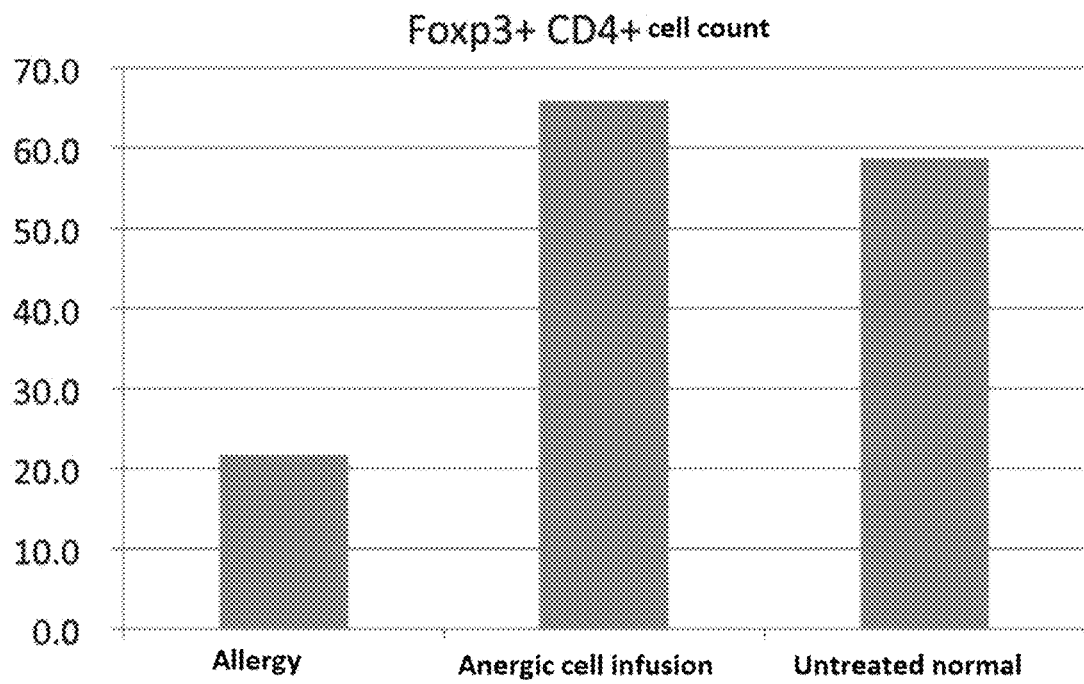
FIG. 15b shows the mean cell count of regulatory T cells (CD4+ FOXP3+) per 1 mm$^2$ obtained from the result of analysis of the images shown in FIG. 14. The graph shows, from the left, food allergy mouse (allergy), anergic cell infused food allergy mouse (anergic cell infusion), and untreated normal mouse (untreated normal).
Figure 15C:
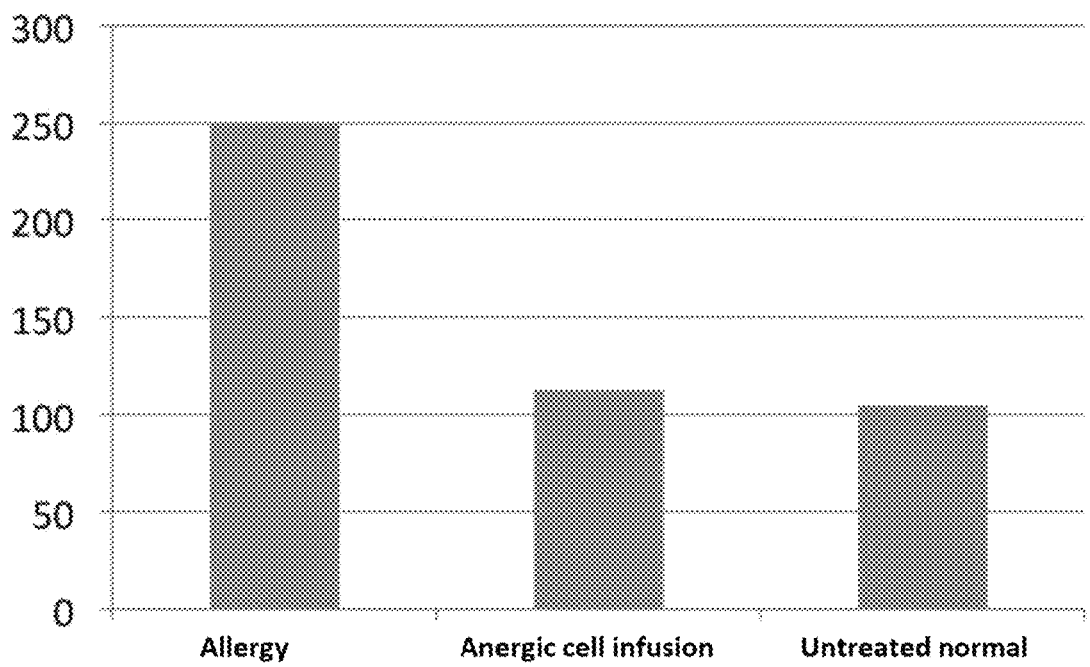
FIG. 15c is a graph showing the mean eosinophil count per 1 mm$^2$ obtained from the result of analysis of the images shown in FIG. 15a. The figure shows, from the left, allergy, anergic cell infusion, and untreated normal in the same manner as FIG. 15b.

The results are shown in FIGS. 14 and 15. FIG. 14 shows results of typical FoxP3/CD4 immunostaining. Allergy developed mice are mice #11 and #12 (3 images of different sites in each intestinal tract), anergic cell infused mice are mice #21 and #22 (3 images of different sites in each intestinal tract), and untreated normal mice were mice #31 and #32 (one each). FIG. 15*a* shows 1 picture of typical HE staining for each mouse. FIG. 15*b* quantifies the results of analyzing the images shown in FIG. 14 and represents the number of reg T cells per 1 mm² as a graph. FIG. 15*c* quantifies the results of analyzing the images shown in FIG. 15*a* and represents the number of eosinophils per 1 mm² as a graph.

As shown in FIG. 15*b*, infiltration of reg T cells is increased in the anergic cell administered group compared to allergy developed group, and more reg T cells are in the intestinal tract wall than in normal mice. Likewise, as shown in FIG. 15*c*, the number of eosinophils, which are considered increased upon allergy, is reduced to the same level as normal mice by infusion of anergic cells. The above results demonstrate that immune tolerance is induced by infusion of anergic cells in food allergy, resulting in induction of decreased infiltration of eosinophils and infiltration of reg T to alleviate the symptoms.

Example 10: Elicitation of Immune Tolerance in iPS Cells

This Example conducted an experiment to demonstrate whether severe immune rejection that occurs in a transplantation experiment using iPS cells and cell/tissue differentiated therefrom can be healed using the anergic cells of the present disclosure. Immune tolerance was elicited in the following manner, which is described below.

(Materials and Methods)

(Neuron Differentiation from iPS Cells to Immune Tolerance Elicitation Experiment)

In accordance with the method already described in a reference (10), iPS cells were differentiated into nerve cells. 30 Gy of radiation (γ ray) was irradiated onto the nerve cells, which were then used as stimulator cells. As responder cells, mononuclear cells (PBMC) obtained from human peripheral blood of volunteers with different MHCs were used. The stimulator cells and responder cells were adjusted with a 2% human type AB serum (pooled) added Biowest ALYS505N-0 medium so that the concentration would each be $2 \times 10^6$ cells/ml, and cultured for 7 days in a 37° C. 5% $CO_2$ incubator in a 12-well plate (Corning, Cat. No. 3513) in the presence of anti-human CD80 antibodies and anti-human CD86 antibodies at 10 µg/mL each in the same manner as Example 1. After 7 days, the cells were collected, and the culture was washed out by centrifugation to obtain anergic cells.

(Evaluation of Immunosuppression Ability)

Anergic cells obtained by co-culture with iPS cell derived nerve cells (stimulator cells) were diluted so that the ratio with respect to newly collected PBMCs of the same volunteer would be 1/2 to 1/16. The cells were added to a mixed culture system (4 well each at $2 \times 10^5$ cells/200 µL/well) on a 96-well plate (Corning, Cat. No. 3799) comprising newly collected identical volunteer derived PBMCs and nerve cells derived from the same iPS cells irradiated with 30 Gy of radiation (γ ray) at a cell count of about 1:1, and cultured in a 37° C. 5% $CO_2$ incubator. On day 4 from the start of culture, ³H-thymidine (10 µL) was added. On day 5 from the start of culture (after 16 to 20 hours from addition of ³H-thymidine), cultured cells were harvested with a Cell Harvester (Molecular Devices). The amount of ³H-thymidine incorporation was measured with a scintillation counter.

(Results)

Figure 16:
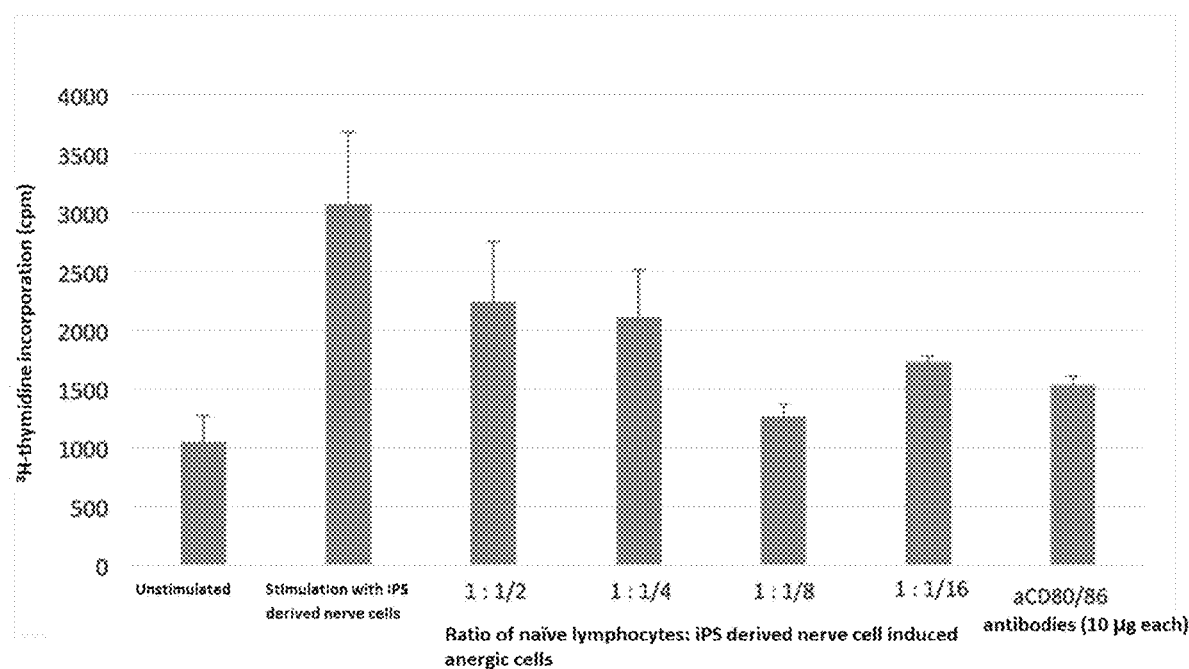
FIG. 16 shows results of eliciting immune tolerance with iPS cells. The graph represents the increase of lymphocytes as a CPM value of the amount of $^3$H-thymidine incorporation. The figure shows reactions of, from the left, only naïve lymphocytes, stimulation with allogenic iPS cell derived nerve cells, cases where iPS derived nerve cells and antibody stimulation induced anergic cells were added to a system of stimulation with allogenic iPS cell derived nerve cells so that the ratio of naïve lymphocytes to anergic cells would be 1:½, 1:¼, 1:⅛, or 1:1/16, and cases where anti-CD80/CD86 antibodies (10 μg/ml) were added to a system of stimulation with allogenic iPS cell derived nerve cells.
Figure 17:
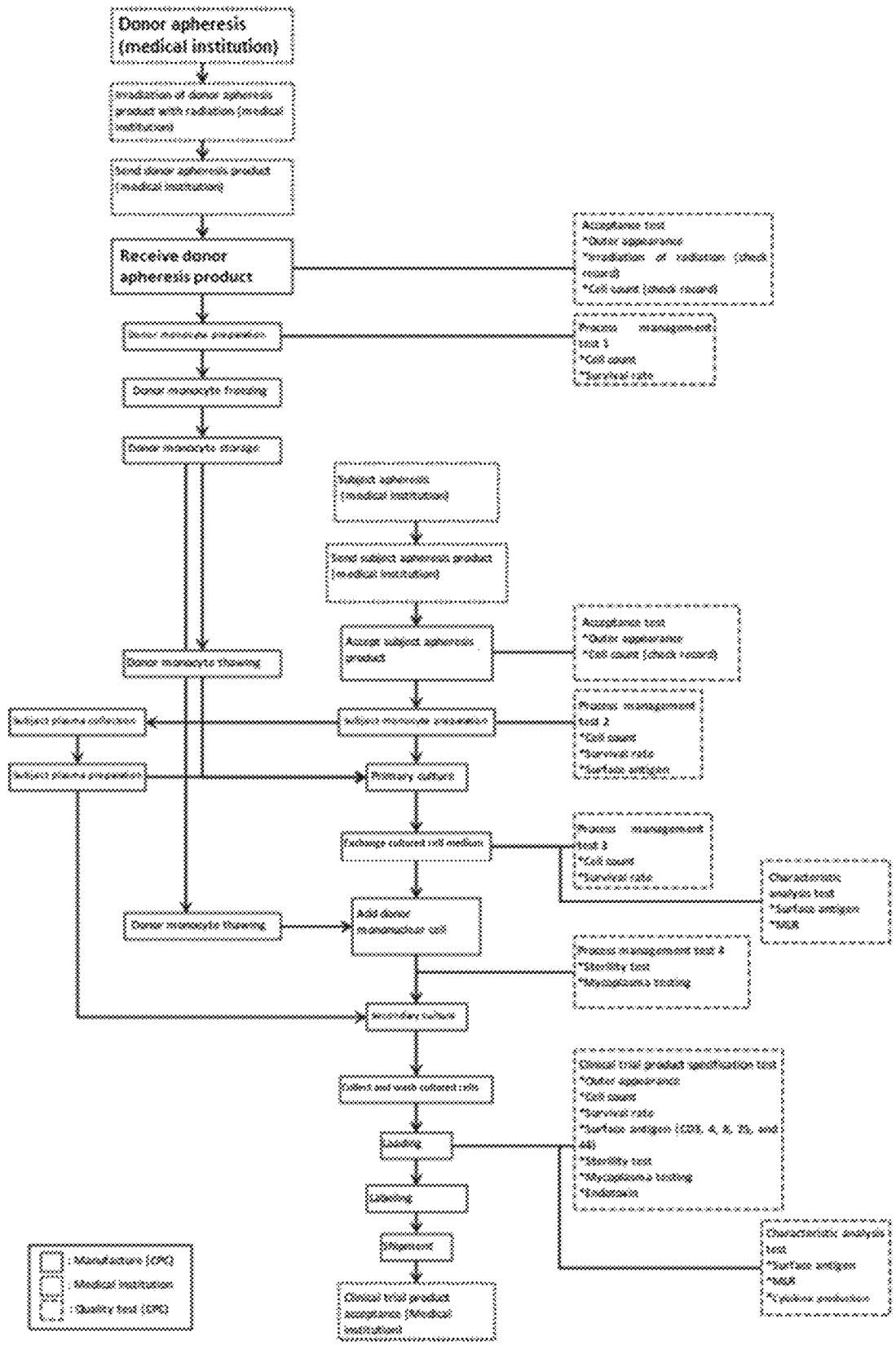
FIG. 17 shows a representative example of the flow of manufacturing and quality testing.

As shown in FIG. 16, nerve cells differentiated from iPS cells stimulate PBMCs of a volunteer with non-matching MHC and induce proliferation. It was shown that anergic cells induced by co-culture of anti-CD80/86 antibodies and nerve cells differentiated from iPS cells suppressed the proliferative response of lymphocytes caused by reacting to nerve cells differentiated from iPS cells in vitro. This demonstrates that the present disclosure can attenuate the immune rejection that occurs in transplantation of cells or tissue derived from iPS cells.

Example 11: Elicitation of Immune Tolerance Using Various Inhibitory Factors This Example shows that immune tolerance can also be elicited using various inhibitory factors.

(Production of Anergic Cells)

Basically, experiments are conducted according to the method described in Example 1 and a method already described in a reference (1 to 3). Recipient PBMCs and donor PBMCs freshly separated from human peripheral blood are used, or those cryopreserved at −80° C. that were rapidly thawed are used. These cells are both adjusted to $4 \times 10^6$ cells/mL in a RPMI 1640 medium (Sigma; R8758-500MK) comprising their own plasma or 10% inactivated fetal bovine serum (FCS) (SIGMA #172012-500ML Lot 11D257 or biosera #FB-1380/500 Lot. 015BS482). Donor PBMCs are irradiated with 20 Gy of radiation. The recipient PBMCs and donor PBMCs are mixed at 1:1. An inhibitory factor (e.g., for each of anti-CD80 antibodies/anti-CD86 antibodies, final concentration of 10 µg/ml; for belatacept (or abatacept), final concentration of 10 µg/ml to 40 µg/ml) is added to the mixture. The mixture is cultured for 7 days in a 37° C. 5% $CO_2$ incubator on a 6 cm petri dish (Greiner CELLSTAR® dish, Cat. No. 628160) (culture volume of 3 to 6 mL) or 10 cm petri dish (Corning, Cat. No. 430167) (culture volume of 10 to 15 mL) (cell density at start of culture is $4 \times 10^6$ cells/mL).

Cultured recipient PBMCs are collected by centrifugation on day 7 from the start of culture and adjusted to $4 \times 10^6$ cells/mL in the medium described above. Newly prepared irradiated donor PBMCs are added to the cultured recipient PBMCs so that the ratio of cell counts would be 2:1, and an inhibitory factor (e.g., of for each anti-CD80 antibodies/anti-CD86 antibodies, final concentration of 5 µg/ml to 10 µg/ml; for belatacept (or abatacept), final concentration of 10 µg/ml to 40 µg/ml) is also added. The cells are cultured for 7 days under the same condition described above (cell density: $4 \times 10^6$ cells/mL).

(Evaluation of the Ability to Suppress Immune Response)

Induced cells were collected by centrifugation on day 14 from the start of culture. A mixed lymphocyte test was conducted in accordance with a method already described in a reference (3). A cell suspension is co-cultured in a 37° C. 5% $CO_2$ incubator. The ability to suppress immune responses can be studied by adding $^3$H-thymidine (10 µl) on day 4 from the start of the co-culture, removing $^3$H-thymidine in the culture on day 5 from the start of the co-culture (16 to 20 hours after the addition of $^3$H-thymidine), and measuring the amount of $^3$H-thymidine incorporation.

Example 12: Quality Control for Cell Formulation

See the descriptions in Examples 1 to 10 for the manufacturing method of a cell formulation. The quality of a cell formulation manufactured in accordance with the Examples is controlled as follows.

Representative examples of quality specification to be met are the following.

TABLE 4

Quality specification of final product

| Item | Shipping upon conducting a clinical trial Tested item | Testing method | Provisional specification value |
|---|---|---|---|
| Confirmation test | Outer appearance | Outer appearance test | Visual inspection | Slightly yellowish white to light yellow cell suspension |
| | Cellular phenotype | Ratio of CD3 positive cells | FCM | ≥50% |
| | | Ratio of CD8 positive CD44 positive cells in CD3 positive cells | FCM | ≥5% |

TABLE 4-continued

Quality specification of final product

| Item | Shipping upon conducting a clinical trial Tested item | Testing method | Provisional specification value |
|---|---|---|---|
| | Ratio of CD4 positive CD44 positive cells in CD3 positive cells | FCM | ≥5% |
| | Ratio of CD4 positive CD25 positive cells in CD3 positive cells | FCM | ≥5% |
| Purity test | Ratio of CD45 positive cells | FCM | ≥95% |
| Safety | Sterility test | Method in Japanese Pharmacopoeia | Growth of microorganism not found |
| | Endotoxin | Method in Japanese Pharmacopoeia | <0.25 EU/ml |
| | Mycoplasma | Method in Japanese Pharmacopoeia | Negative |
| Cell count | Cell count | Hemocytometer | $1 \times 10^8$ to $30 \times 10^8$ cells |
| Viable cell ratio | Viable cell ratio | Trypan-blue | ≥70% |

Cell Formulation Quality Control Test

For example, the following tests are conducted to find whether anergic cells produced in accordance with the descriptions in Examples 1 to 10 meet the quality specification for a final product by the method described herein.

Outer Appearance

The outer appearance of anergic cells suspended in saline is visually inspected. A suspension meeting the quality specification should consist of slightly yellowish white to light yellow cells.

Cellular Phenotype and Purity of Anergic Cells

Anergic cells are analyzed through multiple staining using, for example, the following antibodies to find each phenotype by flow cytometry:

CD3: FITC fluorescence labeled anti-human CD3 antibodies (UCHT1; eBioscience #11-0038-42) or Pacific Blue fluorescence labeled anti-human CD3 antibodies (UCHT1; Invitrogen #CD0328)

CD4: PE fluorescence labeled anti-human CD4 antibodies (RPA-T4; eBioscience #25-0049-42)

CD8: APC fluorescence labeled anti-human CD8 antibodies (RPA-T8; eBioscience #17-0088-42)

CD25: PerCP fluorescence labeled anti-human CD25 antibodies (MEM-181; eBioscience #A15802)

CD44: PE-Cy7 fluorescence labeled anti-human CD44 antibodies (IM7; eBioscience #25-0441-82)

CD45: Brilliant Violet fluorescence labeled anti-human CD45 antibodies (HI30; BioLegend #304032)

CD45RA: FITC fluorescence labeled anti-CD45RA antibodies (ALB11; Beckman Coulter A07786) or PE fluorescence labeled anti-CD45RA antibodies (ALB11; Beckman Coulter IM1834U)

CD45RO: ECD fluorescence labeled anti-CD45RO antibodies (UCHL1; Beckman Coulter IM2712U) or PE fluorescence labeled anti-CD45RO antibodies (UCHL1; Beckman Coulter A07787) or APC fluorescence labeled anti-CD45RO antibodies (UCHL1; Bay biosciences 20-0457)

(Procedure)

Ratio of CD3 positive cells, ratio of CD45 positive cells in viable cells, ratio of CD8 positive CD44 positive cells in CD3 positive cells, ratio of CD4 positive CD44 positive cells in CD3 positive cells, ratio of CD8 positive CD45RA negative cells in CD3 positive cells, ratio of CD8 positive CD45RA negative CD45RO positive cells in CD3 positive cells, ratio of CD4 positive CD45RA negative CD45RO positive cells in CD3 positive cells, and ratio of CD4 positive CD25 positive cells in CD3 positive cells Anergic cells suspended in saline are reacted with the antibody described above and then dead cells are stained using a Zombie NIR Fixable Viability Kit (BioLgened #423106). For cells subjected to multiple fluorescence staining, the ratio of CD3 positive cells in all viable cells is determined in FACS Verse (BD Bioscience).

For anergic cells meeting the quality specification, 50% or more of the cells should be CD3 positive. At the same time, the ratio of CD45 positive cells in viable cells, ratio of CD8 positive CD44 positive cells, ratio of CD4 positive CD44 positive cells, ratio of CD8 positive CD45RA negative cells, ratio of CD8 positive CD45RA negative CD45RO positive cells, ratio of CD4 positive CD45RA negative CD45RO positive cells, and ratio of CD4 positive CD25 positive cells in all live CD3 positive cells are determined based on fluorescence.

For anergic cells meeting the quality specification, 95% or more of viable cells should be CD45 positive, and the cells do not contain a significant amount of impurities such as red blood cells and platelets. Furthermore, anergic cells meeting the quality speciation are cells wherein 5% or more are CD8 positive CD44 positive, 5% or more are CD4 positive CD44 positive cells, 5% or more are CD8 positive CD45RA negative, 5% or more are CD8 positive CD45RA negative CD45RO positive, 5% or more are CD4 positive CD45RA negative CD45RO positive, and 5% or more are CD4 positive CD25 positive cells in the CD3 positive cell population.

Safety

Basically, an experiment is conducted in accordance with the descriptions in the Japanese Pharmacopoeia or a corresponding pharmacopoeia in another country. Exemplary embodiments are detailed hereinafter.

Sterility Testing Method

Anergic cell suspension is lightly centrifuged, and the supernatant thereof is subjected to a sterility test. The direct method, which is a representative sterility test in the Japanese Pharmacopoeia, seeds the supernatant in a soybean/casein/digest medium or liquid thioglycolate medium and cultures the supernatant for 14 days or more at 30 to 35° C. or 20 to 25° C., respectively. The culture is then observed several times during the culture period. Membrane filtration, which is another representative sterility test, dilutes supernatant with a sterile diluent (e.g., 1 g/L of meat or casein peptone solution (pH of 7.1±0.2)), and transfers the diluted supernatant onto a membrane filter for filtration. The membrane filter is then placed in each of the two types of medium described above and cultured for 14 days or more. In a product meeting the quality specification, proliferation of microorganisms is not detected from visual inspection in the medium during the culture period and the final day.

Endotoxin Testing

An anergic cell suspension is diluted as appropriate with saline and adjusted to a pH of 6.0 to 8.0. The endotoxin concentration in a sample is then quantitatively determined by mixing the suspension with a lysate reagent and using gel formation of the lysate reagent as an indicator (gelation method), or using the change in turbidity in the gelling process of the lysate reagent as an indicator (turbidimetry), or using coloring due to hydrolysis of a synthesis substrate s an indicator (colorimetry). A preliminary test for confirming the displayed sensitivity of the lysate reagent is performed as needed. For a product meeting the quality specification, the endotoxin concentration must be less than 0.25 EU/mL.

*Mycoplasma* Test

A culture or anergic cell suspension is lightly centrifuged, and the supernatant thereof is subjected to a *Mycoplasma* test. A culture method, which is a representative *Mycoplasma* test in the Japanese Pharmacopoeia, seeds a sample in an agar plate and cultures the sample for 14 days in nitrogen gas comprising 5 to 10% carbon dioxide gas under a suitable humidity at 35 to 37° C., or seeds a sample in a container comprising a liquid medium and cultures the sample at 35 to 37° C., harvests an aliquot from the liquid culture when a change in the color tone of the liquid medium is observed or at a certain interval from the start of the culture, and seeds the aliquot in a new agar plate to continue culturing. The presence of a colony of *Mycoplasma* is investigated in all agar plates with a microscope at a 100× magnification or greater on day 7 and day 14. The DNA staining method using an indicator cell, which is another representative *Mycoplasma* test, typically uses an indicator cell Vero cell and a designated *Mycoplasma* strain. This method seeds an indicator cell in a culture dish or the like with a cover glass placed therein and allows the cell to proliferate for 1 day at 35 to 38° C. in air containing 5% carbon dioxide gas. A sample (culture or supernatant) is then added, and the culture is continued for 3 to 6 days under the same condition. After immobilizing the cultured cells on the cover glass, DNA fluorescent staining is performed with a stain such as bisbenzimide. The cells are observed with a fluorescence microscope (magnification of 400× to 600× or greater), and a negative (unseeded) control and a *Mycoplasma* positive control are compared therewith. If, while doing so, 0.5% or more of the cells have a minute extranuclear fluorescent spot surrounding the cell nucleus, the cells are deemed *Mycoplasma* positive. A product meeting the quality specification should be *Mycoplasma* negative.

Cell Count

The cell count of anergic cells suspended in saline is taken under a microscope using a hemocytometer or with an automatic cell counter. An anergic cell count that is suitable for administration and meets the quality specification is $1 \times 10^8$ to $30 \times 10^8$ cells (e.g., in 100 mL of saline). If the cell count is below this range, cells should be added as appropriate.

Viable Cell Ratio

Anergic cells suspended in saline are mixed with 0.3 to 0.5% trypan-blue stain (e.g., catalog #35525-02, Nacalai Tesque), and the viable cell count is taken under a microscope using a hemocytometer or with an automatic cell counter. In a product meeting the quality specification, 70% or more of the cells should be viable cells.

These findings can be an important check point in the quality control of a cell formulation for rejection suppression.

MENTIONED REFERENCES

The following Mentioned References were referenced as a fundamental technology in the Examples and the like. It is not acknowledged that these references constitute prior art to the present disclosure. The content thereof is incorporated by reference.
1. Davies J K, Barbon C M, Voskertchian A, Nadler L M, Guinan E C. Ex vivo alloanergization with belatacept: a strategy to selectively modulate alloresponses after transplantation. Cell transplantation. 2012; 21 (9): 2047-61.
2. Davies J K, Gribben J G, Brennan L L, Yuk D, Nadler L M, Guinan E C. Outcome of alloanergized haploidentical bone marrow transplantation after ex vivo costimulatory blockade: results of 2 phase 1 studies. Blood. 2008; 112 (6): 2232-41.
3. Davies J K, Nadler L M, Guinan E C. Expansion of allospecific regulatory T cells after anergized, mismatched bone marrow transplantation. Science translational medicine. 2009; 1 (1): 1ra3.
4. Guinan E C, Boussiotis V A, Neuberg D, Brennan L L, Hirano N, Nadler L M, et al. Transplantation of anergic histoincompatible bone marrow allografts. The New England journal of medicine. 1999; 340 (22): 1704-14.
5. Bashuda H, Kimikawa M, Seino K, Kato Y, Ono F, Shimizu A, et al. Renal allograft rejection is prevented by adoptive transfer of anergic T cells in nonhuman primates. The Journal of clinical investigation. 2005; 115 (7): 1896-902.
6. Bashuda H, Shimizu A, Uchiyama M, Okumura K. Prolongation of renal allograft survival by anergic cells: advantages and limitations. Clin Transplant. 2010; 24 Suppl 22:6-10.
7. Luo Z, Gotoh M, Grochowiecki T, Tanaka T, Kimura F, Kawashima H, et al. Anergic T cells generated in vitro suppress rejection response to islet allografts. Transplantation. 2000; 69 (10): 2144-8.
8. Kamijo S, Takeda H, Tokura T, Suzuki M, Inui K, Hara M, et al. IL-33-mediated innate response and adaptive immune cells contribute to maximum responses of protease allergen-induced allergic airway inflammation. Journal of Immunology. 2013; 190 (9): 4489-99
9. Brandt E B, Strait R T, Hershko D, Wang Q, Muntel E E, Scribner T A, et al. Mast cells are required for experimental oral allergen-induced diarrhea. The Journal of clinical investigation. 2003; 112 (12): 1666-77.
10. Matsumoto T, Fujimori K, Andoh-Noda T, Ando T, Kuzumaki N, Toyoshima M, et al. Functional Neurons Generated from T Cell-Derived Induced Pluripotent Stem Cells for Neurological Disease Modeling. Stem cell reports. 2016; 6 (3): 422-35.

NOTE

As disclosed above, the present disclosure is exemplified by the use of its preferred embodiments. However, it is understood that the scope of the present disclosure should be interpreted based solely on the Claims. It is also understood that any patent, any patent application, and any other references cited herein should be incorporated herein by reference in the same manner as the contents are specifically described herein. The present application claims priority to Japanese Patent Application No. 2018-119003 (filed on Jun. 22, 2018). It is understood that the content thereof (can be the entire document) is incorporated herein by reference. Further, a part of or the entire content of Japanese Patent Application No. 2018-118996 and Japanese Patent Application No. 2018-119001 (both filed on Jun. 22, 2018) and international applications claiming priority thereto is incorporated herein by reference.

INDUSTRIAL APPLICABILITY

The present disclosure provides a pharmaceutical composition comprising a cell having immune tolerance induced that is specific to a specific antigen. Since infectious immune tolerance was confirmed, the present disclosure is applicable to fields that require therapeutic management. A technology that can be utilized in industries (pharmaceutical) related to formulations or the like based on such a technology is provided.

The invention claimed is:

1. A method of eliciting permanent immune tolerance (infectious immune tolerance) to a donor in a subject, the method comprising administering to the subject an effective amount of a cell in which immune tolerance has been induced by a step that comprises mixing (i) an inhibitory factor that can inhibit an interaction between CD80 and/or CD86 and CD28, (ii) a cell derived from the subject, and (iii) an antigen derived from the donor or a composition comprising an antigen from the donor,
    wherein immune tolerance is a state where a specific immune response to a specific antigen is not exhibited or a specific immune response is suppressed, and wherein permanent immune tolerance is a maintenance of immune tolerance to a specific antigen at least for several months, for 1 year, for 3 years, or longer, wherein the method is for suppressing or preventing immune rejection caused by an iPS cell or an ES cell or a cell, tissue, or organ derived therefrom in the subject, and wherein the antigen derived from the donor is an antigen derived from said iPS cell or said ES cell.

2. The method of claim 1, wherein the immune tolerance is immune tolerance elicited in a CD8 positive T cell in the subject.

3. The method of claim 1, wherein the inhibitory factor is selected from a small molecule, a protein, a nucleic acid, a lipid, a saccharide, and a combination thereof.

4. The method of claim 3, wherein the protein is an antibody or a variant thereof, or a cell surface molecule or a variant thereof.

5. The method of claim 4, wherein the variant of the antibody is an antigen binding fragment.

6. The method of claim 4, wherein the variant of the cell surface molecule is a fusion protein.

7. The method of claim 1, wherein the inhibitory factor is selected from an anti-CD80 antibody, an anti-CD86 antibody, a bispecific antibody to CD80 and CD86, an anti-CD28 antibody or an antigen binding fragment thereof, a CTLA4-Ig fusion protein, and a CD28-Ig fusion protein.

8. The method of claim 7, wherein the inhibitory factor is a CTLA4-Ig fusion protein, and wherein the CTLA4-Ig fusion protein is abatacept or belatacept.

9. The method of claim 1 where the method is for treating or preventing a disease, disorder, or condition in the subject wherein the disease, disorder, or condition is caused by an antigen that is not derived from the subject.

10. The method of claim 9, wherein the disease, disorder, or condition is selected from graft rejection, allergy, autoimmune disease, graft-versus-host disease, and immune rejection caused by transplantation of an iPS cell or an ES cell or a cell, tissue, or organ derived therefrom.

11. The method of claim 9, wherein the disease, disorder, or condition is allergy, and wherein the antigen derived from the subject or the antigen that is not derived from the subject is an antigen which is a cause of allergy.

12. The method of claim 11, wherein the antigen which is a cause of allergy is selected from an antigen associated with food, an antigen associated with pollen, an antigen associated with a drug, and an antigen associated with a metal.

13. The method of claim 9, wherein the disease, disorder, or condition is immune rejection caused by transplantation of an iPS cell or an ES cell or a cell, tissue, or organ derived therefrom, and wherein the antigen derived from the subject or the antigen that is not derived from the subject is an antigen derived from said iPS cell or said ES cell.

* * * * *